United States Patent
Gu et al.

(10) Patent No.: US 10,980,992 B2
(45) Date of Patent: Apr. 20, 2021

(54) METHODS AND COMPOSITIONS RELATED TO PHYSIOLOGICALLY RESPONSIVE MICRONEEDLE DELIVERY SYSTEMS

(71) Applicant: NORTH CAROLINA STATE UNIVERSITY, Raleigh, NC (US)

(72) Inventors: Zhen Gu, Raleigh, NC (US); Yanqi Ye, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 100 days.

(21) Appl. No.: 15/999,770

(22) PCT Filed: Feb. 17, 2017

(86) PCT No.: PCT/US2017/018319
§ 371 (c)(1),
(2) Date: Aug. 20, 2018

(87) PCT Pub. No.: WO2017/143153
PCT Pub. Date: Aug. 24, 2017

(65) Prior Publication Data
US 2019/0160272 A1    May 30, 2019

Related U.S. Application Data

(60) Provisional application No. 62/297,346, filed on Feb. 19, 2016.

(51) Int. Cl.
*A61M 37/00* (2006.01)
*A61K 38/28* (2006.01)
(Continued)

(52) U.S. Cl.
CPC ...... *A61M 37/0015* (2013.01); *A61K 9/0021* (2013.01); *A61K 38/28* (2013.01);
(Continued)

(58) Field of Classification Search
CPC ...... A61M 37/0015; A61M 2037/0023; A61M 2037/0061; A61M 2037/0046; A61M 2037/003; A61M 2037/0038
See application file for complete search history.

(56) References Cited

U.S. PATENT DOCUMENTS

| 5,773,255 A | 6/1998 | Laurance et al. |
| 6,256,533 B1 * | 7/2001 | Yuzhakov ......... A61M 37/0015 604/20 |

(Continued)

FOREIGN PATENT DOCUMENTS

WO    2016172320 A1    10/2016

OTHER PUBLICATIONS

International Search Report and Written Opinion in PCT/US2017/018319, dated May 8, 2017. 17 pages.
(Continued)

*Primary Examiner* — Emily L Schmidt
(74) *Attorney, Agent, or Firm* — Meunier Carlin & Curfman LLC

(57) ABSTRACT

Disclosed herein are microneedle devices, kits comprising the microneedle devices, and methods of using the microneedle devices. Specifically, disclosed is a device for transport of a material across a biological barrier of a subject comprising: a plurality of microneedles each having a base end and a tip, with at least one pathway disposed at or between the base end and the tip; a substrate to which the base ends of the microneedles are attached or integrated; and at least one reservoir which is in connection with the base ends of the microneedles array, wherein the reservoir comprises an agent delivery system, wherein the agent delivery system comprises an agent to be transported across the biological barrier, or a means for producing an agent to be
(Continued)

transported across the biological barrier, and a means for detecting a physiological signal from the recipient.

16 Claims, 19 Drawing Sheets

(51) Int. Cl.
| | |
|---|---|
| A61K 9/00 | (2006.01) |
| A61K 38/47 | (2006.01) |
| A61K 38/44 | (2006.01) |
| A61K 47/36 | (2006.01) |
| C12N 5/071 | (2010.01) |

(52) U.S. Cl.
CPC .............. *A61K 38/44* (2013.01); *A61K 38/47* (2013.01); *A61K 47/36* (2013.01); *A61M 37/00* (2013.01); *C12N 5/0677* (2013.01); *C12Y 101/03004* (2013.01); *C12Y 302/01001* (2013.01); *C12Y 302/01003* (2013.01); *A61M 2037/0023* (2013.01); *A61M 2037/0053* (2013.01); *A61M 2202/07* (2013.01); *A61M 2230/201* (2013.01)

(56) References Cited

U.S. PATENT DOCUMENTS

| | | | |
|---|---|---|---|
| 6,334,856 B1 | 1/2002 | Allen et al. | |
| 6,503,231 B1 | 1/2003 | Prausnitz et al. | |
| 2003/0055464 A1* | 3/2003 | Darvish | A61N 1/05 607/40 |
| 2003/0083618 A1* | 5/2003 | Angel | A61M 5/14248 604/141 |
| 2003/0153900 A1 | 8/2003 | Aceti et al. | |
| 2007/0249007 A1* | 10/2007 | Rosero | A61B 5/14546 435/14 |
| 2008/0015494 A1* | 1/2008 | Santini, Jr. | A61M 5/1409 604/65 |
| 2009/0043250 A1 | 2/2009 | Gonnelli | |
| 2010/0119557 A1* | 5/2010 | Boyden | A61P 17/02 424/400 |
| 2011/0039308 A1 | 2/2011 | Slupska et al. | |
| 2011/0306853 A1* | 12/2011 | Black | A61B 5/1468 600/309 |
| 2015/0030641 A1 | 1/2015 | Anderson et al. | |
| 2017/0157036 A1* | 6/2017 | D'Souza | A61K 39/0008 |
| 2018/0353643 A1* | 12/2018 | Ma | A61L 27/54 |

OTHER PUBLICATIONS

International Preliminary Report on Patentability in PCT/US2017/018319, dated Aug. 30, 2018. 14 pages.
Yu et al. "Microneedle-Array-Patches Loaded with Hypoxia-Sensitive Vesicles Provide Fast Glucose-Responsive Insulin Delivery", Proceedings of the National Academy of Sciences, Jul. 7, 2015. vol. 112, pp. 8260-8265.
Ye et al. "Microneedles Integrated with Pancreatic Cells and Synthetic Glucose-Signal 1-4, 16, 17, 19-22, 31-36, r Amplifiers for Smart Insulin Delivery," Advanced Materials, Mar. 1, 2016 (Mar. 1, 2016), vol. 40, 41, 50-57, 61-64. 28, Iss. 16, pp. 3115-3121.
Extended European Search Report issued in corresponding application No. EP17753897.2, dated Sep. 11, 2019, 9 pages.
A. J. Harvey, S. A. Kaestner, D. E. Sutter, N. G. Harvey, J. A. Mikszta, R. J. Pettis, Microneedle-based intradermal delivery enables rapid lymphatic uptake and distribution of protein drugs. Pharmaceutical Research 2010, 28, 107.
A. R. Pepper, B. Gala-Lopez, R. Pawlick, S. Merani, T. Kin, A. M. J. Shapiro, A prevascularized subcutaneous device-less site for islet and cellular transplantation. Nature Biotechnology 2015, 33, 518.
American Diabetes Association, Diabetes Care 2013, 36 Supply 1, S67.
C. C. Lin, K. S. Anseth, Cell-cell communication mimicry with poly (ethylene glycol) hydrogels for enhancing β-cell function. Proceedings of the National Academy of Sciences 2011, 108, 6380.
C. Ricordi, T. B. Strom, Clinical islet transplantation: advances and immunological challenges. Nature Reviews Immunology 2004, 4, 259.
D. H.-C. Chou, M. J. Webber, B. C. Tang, A. B. Lin, L. S. Thapa, D. Deng, J. V. Truong, A. B. Cortinas, R. Langer, D. G. Anderson, Glucose-responsive insulin activity by covalent modification with aliphatic phenylboronic acid conjugates. Proceedings of the National Academy of Sciences 2015, 112, 2401.
D. R. Owens, B. Zinman, G. B. Bolli, Insulins today and beyond. The Lancet 2001, 358, 739.
E. Pedraza, M. M. Coronel, C. A. Fraker, C. Ricordi, C. L. Stabler, Preventing hypoxia-induced cell death in beta cells and islets via hydrolytically activated, oxygen-generating biomaterials. Proceedings of the National Academy of Sciences 2012, 109, 4245.
F. B. Barton, et al., Improvement in outcomes of clinical islet transplantation: 1999-2010. Diabetes Care 2012, 35, 1436.
G. L. Warnock, D. M. Thompson, R. M. Meloche, R. J. Shapiro, Z. Ao, P. Keown, J. D. Johnson, C. B. Verchere, N. Partovi, I. S. Begg, M. Fung, S. E. Kozak, S. O. Tong, K. M. Alghofaili, C. Harris, A multi-year analysis of islet transplantation compared with intensive medical therapy on progression of complications in type 1 diabetes. Transplantation 2008, 86, 1762.
G. Steil, Closed-loop insulin delivery—the path to physiological glucose control. Advanced Drug Delivery Reviews 2004, 56, 125.
H. Yu, X. Qiu, S. P. Nunes, K.-V. Peinemann, Biomimetic block copolymer particles with gated nanopores and ultrahigh protein sorption capacity. Nature Communications 2014, 5.
Hayward RA, Manning WG, Kaplan SH, Wagner EH, Greenfield S. Starting Insulin Therapy in Patients with Type 2 Diabetes: Effectiveness, Complications, and Resource Utilization. JAMA. 1997;278(20):1663-1669. doi:10.1001/jama.1997.03550200039029.
Henry, et al., "Micromachined Needles for the Transdermal Delivery of Drugs," Micro Electro Mechanical Systems, Heidelberg, Germany, pp. 494-98 (Jan. 26-29, 1998.
IDF Diabetes Atlas, 6th edn, International Diabetes Federation 2013.
J. E. Chung, S. Tan, S. J. Gao, N. Yongvongsoontorn, S. H. Kim, J. H. Lee, H. S. Choi, H. Yano, L. Zhuo, M. Kurisawa, J. Y. Ying, Self-assembled micellar nanocomplexes comprising green tea catechin derivatives and protein drugs for cancer therapy. Nature Nanotechnology 2014, 9, 907.
J. E. Shaw, R. A. Sicree, P. Z. Zimmet, Global estimates of the prevalence of diabetes for 2010 and 2030, Diabetes Research and Clinical Practice 2010, 87, 4.
J. Yu, Y. Zhang, Y. Ye, R. DiSanto, W. Sun, D. Ranson, F. S. Ligler, J. B. Buse, Z. Gu, Microneedle-array patches loaded with hypoxia-sensitive vesicles provide fast glucose-responsive insulin delivery. Proceedings of the National Academy of Sciences 2015, 112, 8260.
K. M. Bratlie, R. L. York, M. A. Invernale, R. Langer, D. G. Anderson, Materials for diabetes therapeutics. Advanced Healthcare Materials 2012, 1, 267.
L. Kandra, α-Amylases of medical and industrial importance. Journal of Molecular Structure: THEOCHEM 2003, 666-667, 487.
L. M. Weber, K. N. Hayda, K. Haskins, K. S. Anseth, The effects of cell-matrix interactions on encapsulated β-cell function within hydrogels functionalized with matrix-derived adhesive peptides. Biomaterials 2007, 28, 3004.
Mo et al., Emerging micro- and nanotechnology based synthetic approaches for insulin delivery. Chemical Society Reviews 2014, 43, 3595.
N. Gurung, S. Ray, S. Bose, V. Rai, A broader view: microbial enzymes and their relevance in industries, medicine, and beyond. BioMed Research International 2013, 2013, 19 pages.
O. Veiseh, B. C. Tang, K. A. Whitehead, D. G. Anderson, R. Langer, Managing diabetes with nanomedicine: challenges and opportunities. Nature Reviews Drug Discovery 2014, 14, 45.
O. Veiseh, et al., Size- and shape-dependent foreign body immune response to materials implanted in rodents and non-human primates. Nature Materials 2015, 14, 643.

(56) References Cited

OTHER PUBLICATIONS

O. Veiseh, R. Langer, Diabetes: A smart insulin patch. Nature 2015, 524, 39.

R. Gupta, P. Gigras, H. Mohapatra, V. K. Goswami, B. Chauhan, Microbial α-amylases: a biotechnological perspective. Process Biochemistry 2003, 38, 1599.

R. J. Hickey, A. S. Haynes, J. M. Kikkawa, S.-J. Park, Controlling the self-assembly structure of magnetic nanoparticles and amphiphilic block-copolymers: from micelles to vesicles. Journal of the American Chemical Society 2011, 133, 1517.

R. Nishimura, M. Goto, S. Sekiguchi, K. Fujimori, A. Ushiyama, S. Satomi, Assessment for Revascularization of Transplanted Pancreatic Islets at Subcutaneous Site in Mice with a Highly Sensitive Imaging System. Transplantation Proceedings 2011, 43, 3239.

S. Merani, C. Toso, J. Emamaullee, A. M. J. Shapiro, Optimal implantation site for pancreatic islet transplantation. British Journal of Surgery 2008, 95, 1449.

S. Mitragotri, D. G. Anderson, X. Chen, E. K. Chow, D. Ho, A. V. Kabanov, J. M. Karp, K. Kataoka, C. A. Mirkin, S. H. Petrosko, J. Shi, M. M. Stevens, S. Sun, S. Teoh, S. S. Venkatraman, Y. Xia, S. Wang, Z. Gu, C. Xu, Accelerating the translation of nanomaterials in biomedicine. ACS Nano 2015, 9, 6644.

S. P. Sullivan, D. G. Koutsonanos, M. del Pilar Martin, J. W. Lee, V. Zarnitsyn, S.-O. Choi, N. Murthy, R. W. Compans, I. Skountzou, M. R. Prausnitz, Dissolving polymer microneedle patches for influenza vaccination. Nature Medicine 2010, 16, 915.

S. Peat, W. J. Whelan, W. R. Rees, D-enzyme: a disproportionating enzyme in potato juice. Nature 1953, 172, 158.

J. F. Robyt, D. French, Multiple attack hypothesis of α-amylase action: action of porcine pancreatic, human salivary, and Aspergillus oryzae α-amylases. Archives of Biochemistry and Biophysics 1967, 122, 8.

S. Schneider, P. J. Feilen, F. Brunnenmeier, T. Minnemann, H. Zimmermann, U. Zimmermann, M. M. Weber, Long-term graft function of adult rat and human islets encapsulated in novel alginate-based microcapsules after transplantation in immunocompetent diabetic mice. Diabetes 2005, 54, 687.

V. Ravaine, C. Ancla, B. Catargi, Chemically controlled closed-loop insulin delivery. Journal of Controlled Release 2008, 132, 2-11.

W. J. Whelan, P. J. Roberts, Action of salivary α-amylase on amylopectin and glycogen. Nature 1952, 170, 748.

W. Tai et al., Bio-inspired synthetic nanovesicles for glucose-responsive release of insulin. Biomacromolecules 2014, 15, 3495.

Hong et al., Dissolving and biodegradable microneedle technologies for transdermal sustained delivery of drug and vaccine. Drug Design, Development and Therapy 2013, 945.

Y. Seki, T. Nakamura, Y. Okami, Accumulation of 2-aminoimidazole by *Streptomyces eurocidicus*. Journal of biochemistry 1970, 67, 389.

Z. Gu, A. A. Aimetti, Q. Wang, T. T. Dang, Y. Zhang, O. Veiseh, H. Cheng, R. S. Langer, D. G. Anderson et al., Injectable nano-network for glucose-mediated insulin delivery. ACS Nano 2013, 7, 4194.

Z. Gu, A. Biswas, M. Zhao, Y. Tang, Tailoring nanocarriers for intracellular protein delivery. Chemical Society Reviews 2011, 40, 3638.

Zimmermann, Heiko, Stephen G. Shirley, and Ulrich Zimmermann. "Alginate-based encapsulation of cells: past, present, and future." Current diabetes reports 7.4 (2007): 314-320.

\* cited by examiner

METHODS AND COMPOSITIONS RELATED TO PHYSIOLOGICALLY RESPONSIVE MICRONEEDLE DELIVERY SYSTEMS

CROSS-REFERENCE TO RELATED APPLICATIONS

This application claims benefit of U.S. Provisional Application No. 62/297,346, filed Feb. 19, 2016, which is hereby incorporated herein by reference in its entirety.

BACKGROUND OF THE INVENTION

Diabetes mellitus, as one of the most challenging chronic diseases, currently affects over 387 million people worldwide and this number is estimated to increase to around 500 million by 2030 (J. E. Shaw et al. Diabetes Research and Clinical Practice 2010, 87, 4; B. Belgium, *IDF Diabetes Atlas*, 6th edn, International Diabetes Federation 2013). Providing lifelong exogenous insulin is essential for the treatment of type 1 diabetes (Matriano et al. Diabetes Care 2013, 36 Supply 1, S67; R. A. Hayward, Jama 1997, 278, 1663; D. R. Owens, B. Zinman, G. B. Bolli, The Lancet 2001, 358, 739; R. A. Hayward, Jama 1997, 278, 1663; D. R. Owens et al. The Lancet 2001, 358, 739). However, there was an estimated 4.9 million diabetes related deaths worldwide in 2014. A key constraint of the traditional insulin injection lies in inadequate glycemic control, which leads to diabetes complications, such as blindness, limb amputation and kidney failure. Conversely, overtreatment with insulin causes hypoglycemia, which can lead to behavioral and cognitive disturbance, seizure, brain damage, or death (Mo et al. Chemical Society Reviews 2014, 43, 3595; C. Ricordi et al. Nature Reviews Immunology 2004, 4, 259; G. Steil, Advanced Drug Delivery Reviews 2004, 56, 125; Z. Gu et al. Chemical Society Reviews 2011, 40, 3638).

Transplantation of insulin-producing cells has been intensively explored for treating type 1 diabetes (S. Schneider et al. Transplantation 2008, 86, 1762). However, due to the host recognition of transplanted cells, dependence on donor cells and requirement of extensive immunosuppressive therapy, direct cell implantation has a limited role in diabetes care (S. Merani et al. British Journal of Surgery 2008, 95, 1449; R. Nishimura et al. Transplantation Proceedings 2011, 43, 3239; A. R. Pepper et al. Nature Biotechnology 2015, 33, 518). An alternative technique is to encapsulate pancreatic β-cells in a semi-permeable container, isolating and protecting them from the immune system while still allowing the diffusion and transportation of nutrients and oxygen to the encapsulated cells (H. Zimmermann et al. Current Diabetes Reports 2007, 7, 314; E. Pedraza et al., Proceedings of the National Academy of Sciences 2012, 109, 4245; C. C. Lin et al. Proceedings of the National Academy of Sciences 2011, 108, 6380). Nevertheless, the cell-capsule implantation or withdrawal usually requires a surgical procedure. More importantly, biocompatibility of the cell capsules is often compromised resulting in persistent inflammation, formation of foreign body giant cells, fibrosis, damage to the surrounding tissues and failure of the implant to control glucose (O. Veiseh, R. Langer, Nature 2015, 524, 39; Z. Gu, A. A. Aimetti, Q. Wang, T. T. Dang, Y. Zhang, O. Veiseh, H. Cheng, R. S. Langer, D. G. Anderson et al. ACS Nano 2013, 7, 4194; W. Tai et al. Biomacromolecules 2014, 15, 3495). What is needed in the art is a device and method for delivering compositions to a subject in need thereof, wherein the device and method do not require surgery.

BRIEF DESCRIPTION OF THE DRAWINGS

FIG. 1A shows that without GSA, there is insignificant insulin release from the MN patch neither in normoglycemia nor hyperglycemia state. The MN patch is composed of crosslinked hyaluronic acid (grey). FIG. 1B shows that with GSA, there is significant promoted insulin release triggered by a hyperglycemia state. The MN patch is composed of crosslinked hyaluronic acid embedding assembled layers of (from top to bottom) α-amylose and GSA.

FIG. 2A shows TEM images of enzymes-encapsulated GSA pre-, post-incubated in 400 mg/dL glucose solution for 20 minutes, 2 hours and 6 hours at 37° C. respectively. Scale bar is 200 nm. FIG. 2B (top) shows fluorescence 2.5D images of FITC-GA loaded GSA solution pre- and post-incubated in 400 mg/dL glucose solution for 2 hours at 37° C. FIG. 2B (bottom) shows distribution of the fluorescence intensity along the indicated white dash line. (a.u. represents "arbitrary unit"). FIG. 2C shows the size distribution of GSA pre- and post-incubated in 400 mg/dL glucose solution for 6 hours. FIG. 2D shows phosphorescence lifetime profile for the GSA incubated in different glucose level solutions containing an oxygen concentration molecule probe. FIG. 2E shows phosphorescence lifetime profile for the GSA loaded with full or half dose of GOx in 400 mg/dL glucose solutions. FIG. 2F shows the intensity of UV absorption at 330 nm of GSA in solutions with different glucose concentrations at 37° C. Error bars indicate standard deviation (s.d.) (n=3).

FIG. 3A shows in vitro accumulated enzymes release profile of the GSA in solutions with different glucose concentrations at 37° C. *P<0.05 for GSA in 400 mg/dL glucose solution compared with those in 100 or 0 mg/dL glucose concentration solutions. FIG. 3B shows glucose production from the α-amylose hydrolysis catalyzed by the released enzymes. *P<0.05 for GSA in 400 mg/dL glucose solution compared with those in 100 or 0 mg/dL glucose solutions. FIG. 3C shows secretion rate profile of L-S GRS simulated by the inflow of different glucose solutions through a microfluidics device (100 and 400 mg/dL). (n=3). FIG. 3D shows immunofluorescence image of the pancreatic β-cell capsules stained with insulin (green) and nucleus (blue). Scale bar is 500 μm. FIG. 3E (a-c) shows fluorescence images of the pancreatic β-cells from day 1 to day 3 after the encapsulation. Cells were stained with calcium-AM (live, green) and ethidium homodimer (dead, red). Scale bar is 500 μm. (bottom right) The insulin secretion index of the cells capsules as the function of time from day 1 to day 3 after encapsulation. Error bars indicate s.d. (n=3). FIG. 3F shows a schematic of stimulated insulin secretion from the L-S GRS using a microfluidics device. KRB with different glucose concentration flowed through the microfluidics channel and insulin secreted by the pancreatic β-cell capsules was collected from the outlet. FIG. 3G shows pictures of the GSA-loaded MN patch. Scale bar is 1 cm. FIG. 3H shows SEM image of the MN patch. Scale bar is 500 μm. FIG. 3I shows fluorescence microscopy image of the L-S GRS: MN patch was loaded with rhodamine-labeled GSA and calcium AM-stained pancreatic β-cell capsules were positioned on the back of the MN patch. Scale bar is 500 μm.

FIG. 4A shows mouse dorsum skin was transcutaneously treated with MN patches. Scale bar is 1 mm (top); H&E stained cross-section of the treated skin indicated by the area within black dashed line (bottom). The regions of skin muscles and fat tissues are labeled as M and F, respectively. Scale bar is 200 μm. FIG. 4B shows in vivo studies of the MN patches for STZ-induced type 1 diabetic mice treatment. Mice were subjected to transcutaneous administration with a variety of MNs samples: empty MNs without GRS (w/o GRS), MNs integrated with only L-GRS (L-GRS), MNs integrated with only S-GRS (S-GRS), MNs integrated with L-S-GRS (L-S GRS), MNs integrated with L-S-GRS but without GOx in S-GRS (L-S GRS (w/o GOx)), and MNs integrated with L-S-GRS but without α-amylose in S-GRS (L-S GRS (w/o AM)). *$P<0.05$ for administration with MN integrated with L-S GRS compared with the control groups. FIG. 4C shows a change of BGLs of diabetic mice treated with additional MN (L-S GRS) 6 hours post administration. *$P<0.05$ for additional administration with MN compared with no additional administration. The black arrows indicate the administration points. FIG. 4D shows a change of BGLs of healthy mice after the MN administration (MN L-S GRS or empty MN (MN w/o GRS)). Error bars indicate s.d. (n=5). FIG. 4E shows a tolerance test toward diabetic mice 2 hours post administration of MNs with L-S GRS in comparison with the healthy control mice. The time points of administration were pointed out by the black arrows. FIG. 4F shows responsiveness was calculated based on the area under the curve (AUC) in 120 minutes, with the baseline set at the 0-minute blood glucose reading. Error bars indicate s.d. (n=5). *$P<0.05$ for diabetic mice treated with MN L-S GRS administration compared to the healthy mice.

SUMMARY OF THE INVENTION

Figure 1A:
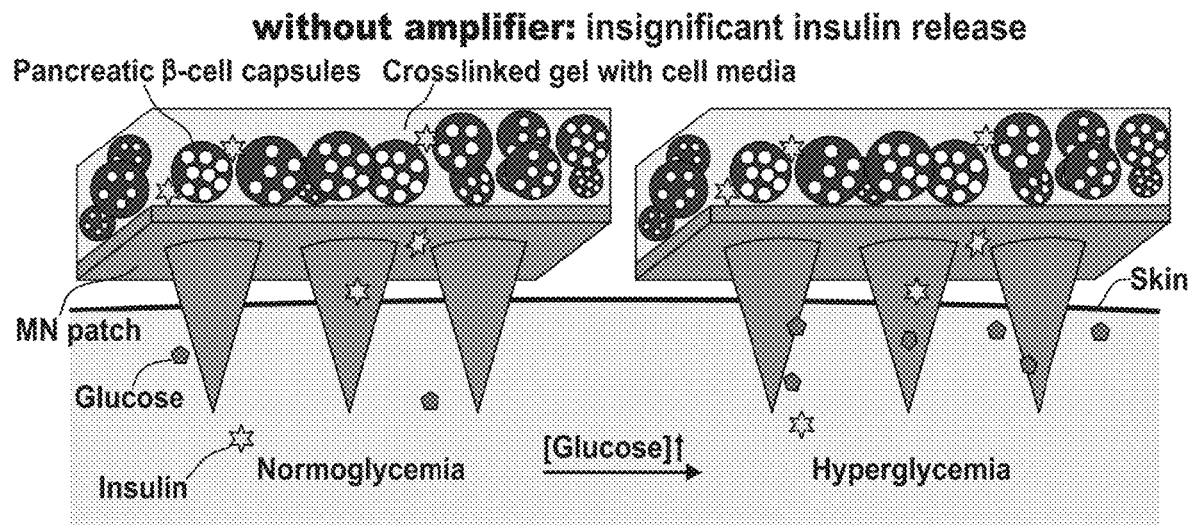
FIGS. 1A and 1B show a schematic of the glucose responsive system (GRS) based on a microneedle-array patch integrated with pancreatic β-cells and glucose signal amplifiers (GSA).

Disclosed herein is a device for transport of a material across a biological barrier of a subject comprising: a plurality of microneedles each having a base end and a tip, with at least one pathway disposed at or between the base end and the tip; a substrate to which the base ends of the microneedles are attached or integrated; at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal from the recipient; and a signal amplifier system, wherein the signal amplifier system comprises a component capable of amplifying the physiological signal from the recipient.

Also disclosed herein is a device for transport of a material across a biological barrier of a subject comprising: a plurality of microneedles each having a base end and a tip, with at least one pathway disposed at or between the base end and the tip; a substrate to which the base ends of the microneedles are attached or integrated; at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal, wherein the agent delivery system comprises a feedback component, such that volume or amount of the agent to be transported across the biological barrier can be altered based on the physiological signal.

Further disclosed herein is a method of treating a disease in a subject in need thereof, the method comprising: a) providing a microneedle patch to the subject, wherein the microneedle patch comprises: i) a plurality of microneedles each having a base end and a tip; ii) a substrate to which the base ends of the microneedles are attached or integrated; iii) at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal from the recipient; and iv) a signal amplifier system, wherein the signal amplifier system comprises a component capable of amplifying the physiological signal from the recipient; b) inserting the microneedles into the biological barrier; and c) delivering the agent through the microneedles and into the biological barrier, wherein the amount or volume of agent delivered is determined by a signal received from the signal amplifier system.

Also disclosed herein is a method of treating a disease in a subject in need thereof, the method comprising: a) providing a microneedle patch to the subject, wherein the microneedle patch comprises: i) a plurality of microneedles each having a base end and a tip; ii) a substrate to which the base ends of the microneedles are attached or integrated; iii) at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal, wherein the agent delivery system comprises a feedback component, such that volume or amount of the agent to be transported across the biological barrier can be altered based on the physiological signal; and b) inserting the microneedles into the biological barrier; and c) delivering the agent through the microneedles and into the biological barrier, wherein the amount or volume of agent delivered is based on the physiological signal.

Disclosed herein is a kit of parts for delivering a therapeutic, prophylactic or diagnostic agent across a biological barrier comprising: a) a microneedle patch comprising a plurality of microneedles each having a base end and a tip, and a substrate to which the base ends of the microneedles are attached or integrated; b) at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal from the recipient; and c) a signal amplifier system, wherein the volume or amount of agent to be transported is altered based on a signal received from the signal amplifier system.

Also disclosed herein is a kit of parts for delivering a therapeutic, prophylactic or diagnostic agent across a biological barrier comprising: a) a microneedle patch comprising a plurality of microneedles each having a base end and a tip, and a substrate to which the base ends of the microneedles are attached or integrated; b) at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal from the recipient.

DETAILED DESCRIPTION OF THE INVENTION

Definitions

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Activities" of a protein, including those relating to "bioactivity," include, for example, transcription, translation, intracellular translocation, secretion, phosphorylation by kinases, cleavage by proteases, and/or homophilic and heterophilic binding to other proteins.

"Biocompatible" generally refers to a material and any metabolites or degradation products thereof that are generally non-toxic to the recipient and do not cause any significant adverse effects to the subject.

A "composition" is intended to include a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

An "effective amount" is an amount sufficient to effect beneficial or desired results. An effective amount can be administered in one or more administrations, applications or dosages.

As used herein, the term "high glucose conditions" refers to an environment having a glucose concentration greater than or equal to 200 mg/dL. For example, "high blood glucose levels" refer to glucose levels in the blood stream greater than or equal to 200 mg/dL. In some embodiments, high glucose conditions are 200-400 mg/dL. In other embodiments, high glucose conditions are 300-400 mg/dL.

As used herein, the term "low glucose conditions" refers to an environment having a glucose concentration from 0 to 200 mg/dL. For example, "low blood glucose levels" refer to glucose levels in the blood stream less than 200 mg/dL.

The terms "peptide," "protein," and "polypeptide" are used interchangeably to refer to a natural or synthetic molecule comprising two or more amino acids linked by the carboxyl group of one amino acid to the alpha amino group of another.

The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "therapeutically effective amount" or "therapeutically effective dose" refer to the amount of a composition, such as glucose-modified insulin bound to a glucose-binding structure, that will elicit the biological or medical response of a tissue, system, animal, or human that is being sought by the researcher, veterinarian, medical doctor or other clinician over a generalized period of time. In some embodiments, a desired response is the control of type I diabetes. In some instances, a desired biological or medical response is achieved following administration of multiple dosages of the composition to the subject over a period of days, weeks, or years.

The term "subject" or "recipient" is defined herein to include animals such as mammals, including, but not limited to, primates (e.g., humans), cows, sheep, goats, horses, dogs, cats, rabbits, rats, mice and the like. In some embodiments, the subject is a human.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

In some instances, the terms "treat", "treating," "treatment" and grammatical variations thereof, include controlling blood sugar levels and reducing the severity of type I diabetes symptoms as compared with prior to treatment of the subject or as compared with the incidence of such symptom in a general or study population.

The term "type I diabetes" refers to the form of diabetes mellitus resulting from the autoimmune destruction of insulin-producing cells and reduction of the body's ability to produce insulin. The loss of insulin results in increased blood sugar.

Detailed Description

Disclosed herein is a device for transport of a material across a biological barrier of a subject comprising:

a plurality of microneedles each having a base end and a tip, with at least one pathway disposed at or between the base end and the tip;

a substrate to which the base ends of the microneedles are attached or integrated; and at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal from the recipient.

The agent delivery system can, for example, comprise a feedback component, such that volume or amount of the agent to be transported across the biological barrier can be altered based on the physiological signal. The feedback component can comprise an "on and off" switch, such that when a signal is detected, the agent delivery system can deliver an agent to the recipient, but when no signal is detected, no agent is delivered. Conversely, the detection of a signal can have the opposite effect, wherein the agent delivery system defaults to delivery of an agent to the recipient, unless a signal is detected, which causes the agent delivery system not to release an agent for delivery to the recipient. By way of illustration, the feedback component can detect the presence of a pathogen in the recipient (the agent), and when the agent is detected, the feedback component can allow for the release of an antibody from the reservoir.

In another example, the feedback component can detect changes in a physiological signal, such as pH or temperature. The feedback component can comprise a "cut off value" such that when the pH or the temperature changes by a certain amount, or reaches a certain numerical value (a pH below 6.5, for example, or a temperature above 99.1, for example), the feedback component allows for a change in the release of the agent, or the amount of the agent released, and subsequently administered to the recipient.

The feedback component can also adjust the amount or volume of the agent released based on the amount of signal detected, so that a greater amount of signal detected can result in a greater amount of agent released, or conversely, a greater amount of signal detected can result in a smaller amount of agent released.

Optionally, the device can comprise a signal amplifier system, wherein the signal amplifier system comprises a component capable of amplifying the physiological signal from the recipient. The signal amplifier system works by increasing the signal, which increases the signal detected by the agent delivery system. This can be done in the case where there is a need to detect very small changes in the physiological signal, or when the agent delivery system is not sensitive enough to detect a change without amplification of the signal. An example of a signal amplifier system can be found in Example 1.

The signal amplifier system can be integrated within the microneedles. For example, the signal amplifier system can be in the tips of the microneedles, either as a coating on the outside of the microneedle, or inside the tips of the microneedle.

The physiological signal detected can, in one aspect, be any substance present in the recipient. For example, the physiological signal can be a biological substance or a drug. The substance can either occur naturally in the recipient, or can be a non-endogenous, or foreign, substance. In another aspect, the physiological response in the subject can comprise physiological environment factors, including pH and temperature. Examples of physiological signals include, but are not limited to, glucose, cholesterol, bilirubin, creatine, metabolic enzymes, hemoglobin, heparin, clotting factors, uric acid, carcinoembryonic antigen or other tumor antigens, reproductive hormones, oxygen, pH, temperature, alcohol, tobacco metabolites, and illegal drugs.

The agent in the reservoir to be delivered to the recipient can be a therapeutic, prophylactic, or diagnostic agent. For example, the agent can be selected from the group consisting of peptides, proteins, carbohydrates, nucleic acid molecules, lipids, organic molecules, biologically active inorganic molecules, and combinations thereof. For example, a wide range of drugs may be formulated for delivery with the present microneedle devices and methods. As used herein, the terms "drug" or "drug formulation" are used broadly to refer to any prophylactic, therapeutic, or diagnostic agent, or other substance that which may be suitable for introduction to biological tissues, including pharmaceutical excipients and substances for tattooing, cosmetics, and the like. The drug can be a substance having biological activity. The drug formulation may include various forms, such as liquid solutions, gels, solid particles (e.g., microparticles, nanoparticles), or combinations thereof. The drug may comprise small molecules, large (i.e., macro-) molecules, or a combination thereof. In representative, not non-limiting, embodiments, the drug can be selected from among amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, and viruses. The drug may be selected from suitable proteins, peptides and fragments thereof, which can be naturally occurring, synthesized or recombinantly produced. In one embodiment, the drug formulation includes insulin.

The drug formulation may further include one or more pharmaceutically acceptable excipients, including pH modifiers, viscosity modifiers, diluents, etc., which are known in the art. Specifically, the agent can be insulin.

The device disclosed herein can comprise the agent for release itself, or a means for producing an agent to be transported across the biological barrier reservoir. One example of a means for producing an agent is cells. The cells can be mammalian cells, such as human cells, or can be cells from any other source, which are capable of producing an agent for administration to a recipient. For example, the cells can pancreatic β cells or stem cell-differentiated human pancreatic cells.

The agent, or the means for producing the agent, can be disposed in a reservoir which is semi-permeable, for example. This can allow for the exchange of fluid with the recipient, such that the feedback component can be in fluid communication with the recipient, and thereby detect changes in physiological signal of the recipient. For example, the reservoir can comprise cells, wherein the cells are sensitive to changes in a physiological signal from the recipient. Such physiological changes in the recipient can stimulate the cells to release an agent, or to stop releasing an agent, as described above in regard to the feedback component. In one example, the reservoir can comprise an alginate microgel.

In one example, the signal amplifier system comprises a glucose signal amplifier (referred to as a "GSA" herein). The signal amplifier system can comprise self-assembled polymeric nanosized vesicles. By way of specific example, the glucose signal amplifier can comprise glucose oxidase, α-amylase, and glucoamylase.

In regard to the microneedles themselves, they can be constructed from a variety of materials, including metals, ceramics, semiconductors, organics, polymers, and composites. Preferred materials of construction include pharmaceutical grade stainless steel, gold, titanium, nickel, iron, tin, chromium, copper, palladium, platinum, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polyester, and polyacrylamides.

The microneedles should have the mechanical strength to remain intact while being inserted into the biological barrier, while remaining in place for up to a number of days, and while being removed. In embodiments where the microneedles are formed of biodegradable polymers, the microneedle must to remain intact at least long enough for the microneedle to serve its intended purpose (e.g., its conduit function for delivery of drug). The microneedles should be sterilizable using standard methods such as ethylene oxide or gamma irradiation.

The microneedles can have straight or tapered shafts. In a preferred embodiment, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, i.e. they may simply be cylinders with blunt or flat tips. A hollow microneedle that has a substantially uniform diameter, but which does not taper to a point, is referred to herein as a "microtube." As used herein, the term "microneedle" includes both microtubes and tapered needles unless otherwise indicated.

The microneedles can be oriented perpendicular or at an angle to the substrate. Preferably, the microneedles are oriented perpendicular to the substrate so that a larger density of microneedles per unit area of substrate can be provided. An array of microneedles can include a mixture of microneedle orientations, heights, or other parameters.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The cross-sectional dimensions can be between about 1 μm and 1000 μm, such that the base can be about 200-600 μm, and the tip can be between 1 and 20 μm. In one embodiment, the microneedle can be approximately 400 μm at the base, and approximately 5 μm at the tip.

The length of the microneedles typically is between about 10 μm and 1 mm, preferably between 400 μm and 1 mm. For example, the length of the microneedle can be approximately 800 µm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles.

The reservoir can be connected to the tip of the microneedle, such that an agent stored or produced in the reservoir can flow from the reservoir and out through the microneedle tip, into the target tissue. The reservoir is to provide suitable, leak-free storage of the agent, or the means of producing the agent, before it is to be delivered.

The reservoir of a single microneedle device can include a plurality of compartments that are isolated from one another and/or from a portion of the microneedles in an array. The device can, for example, be provided to deliver different agents through different needles, or to deliver the same or different agents at different rates or at different times. Alternatively, the contents of the different compartments can be combined with one another, for example, by piercing, or otherwise removing, a barrier between the compartments, so as to allow the materials to mix.

The microneedle and substrate are made by methods known to those skilled in the art. Examples include microfabrication processes, by creating small mechanical structures in silicon, metal, polymer, and other materials. Three-dimensional arrays of hollow microneedles can be fabricated, for example, using combinations of dry etching processes; micromold creation in lithographically-defined polymers and selective sidewall electroplating; or direct micromolding techniques using epoxy mold transfers. These methods are described, for example, in U.S. Ser. No. 09/095,221, filed Jun. 10, 1998; U.S. Ser. No. 09/316,229, filed May 21, 1999; Henry, et al., "Micromachined Needles for the Transdermal Delivery of Drugs," Micro Electro Mechanical Systems, Heidelberg, Germany, pp. 494-98 (Jan. 26-29, 1998).

Also disclosed herein are methods of treating a disease in a subject in need thereof, the method comprising:
  a) providing a microneedle patch to the subject, wherein the microneedle patch comprises:
    i) a plurality of microneedles each having a base end and a tip;
    ii) a substrate to which the base ends of the microneedles are attached or integrated;
    iii) at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal from the recipient; and;
  b) inserting the microneedles into the biological barrier; and
  c) delivering the agent through the microneedles and into the biological barrier, wherein the amount or volume of agent delivered is determined by a signal received from the signal amplifier system.

As discussed above, the agent delivery system can, for example, comprise a feedback component, such that volume or amount of the agent to be transported across the biological barrier can be altered based on the physiological signal. The feedback component can essentially comprise an "on and off" switch, such that when a signal is detected, the agent delivery system can deliver an agent to the recipient. Conversely, the detection of a signal can have the opposite effect, thereby causing the agent delivery system not to release an agent for delivery to the recipient. By way of illustration, the feedback component can detect the presence of a pathogen in the recipient, and when the analyte is detected, the feedback component can allow for the release of an antibody from the reservoir.

Also discussed above, the device can comprise a signal amplifier system, wherein the signal amplifier system comprises a component capable of amplifying the physiological signal from the recipient. The signal amplifier system works by increasing the signal, which increases the signal detected by the agent delivery system. This can be done in the case where there is a need to detect very small changes in the physiological signal, or when the agent delivery system is not sensitive enough to detect a change without amplification of the signal. An example of a signal amplifier system can be found in Example 1.

Also disclosed herein are kits. The kits can include parts for use with the methods disclosed herein. For example, the kits can comprise the parts needed to form the devices disclosed herein. Disclosed is a kit of parts for delivering a therapeutic, prophylactic or diagnostic agent across a biological barrier comprising: a) a microneedle patch comprising a plurality of microneedles each having a base end and a tip, and a substrate to which the base ends of the microneedles are attached or integrated; b) at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal from the recipient. The agent delivery system can further comprise a feedback component. Also disclosed as part of the kit can be a signal amplifier system, which is discussed herein. The kit can also comprise written instructions for use.

EXAMPLES

Example 1

Microneedle Patch Platform

Figure 1B:
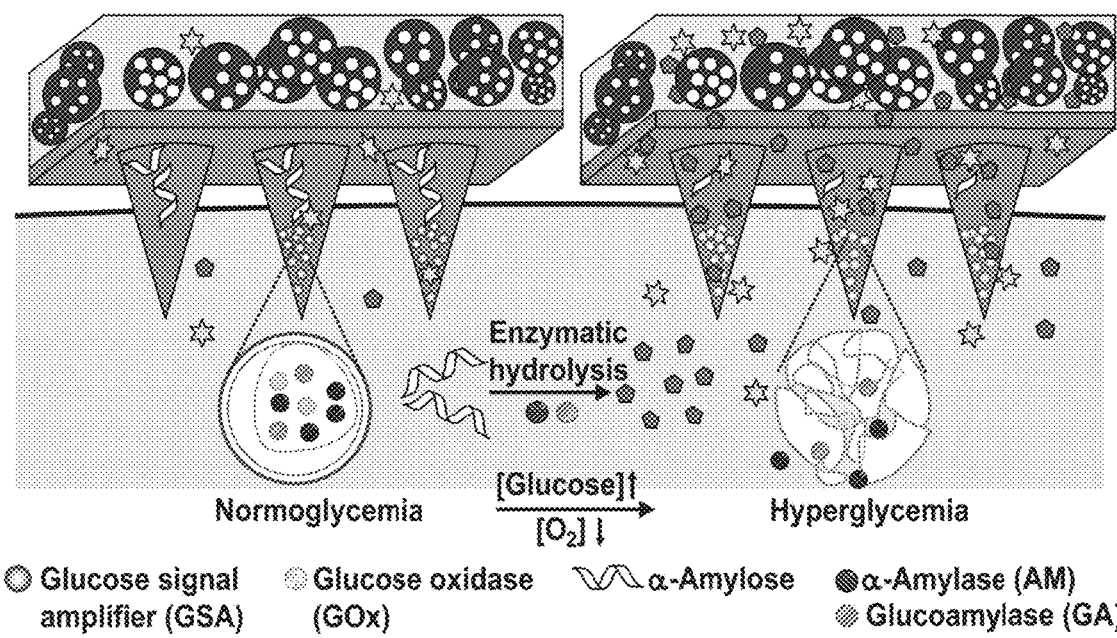

Disclosed herein is a painless microneedle (MN) patch platform to modulate the insulin secretion from pancreatic β-cells for glucose-responsive regulation of blood glucose levels (BGLs) without implantation. As shown in FIG. 1, this strategy integrates both live (cell-based) and synthetic glucose-responsive systems (L-S GRS) to allow the externally positioned β-cell capsules to sense glucose signals and to secrete insulin through the MN in a minimally invasive manner. The initial design integrated cell capsules with the MN patch made from the crosslinked hyaluronic acid (HA) (FIG. 1a). It was expected that under a hyperglycemic state, glucose could diffuse through the MN and interact with β-cells encapsulated in the alginate microgels in order to promote insulin secretion. However, due to the limited diffusion of glucose, the patch did not effectively respond to a hyperglycemic state and an insignificant increase in insulin secretion was detected. To effectively trigger the cellular response, the MN matrix reported here specifically contains synthetic "glucose-signal amplifiers" (GSAs) (FIG. 1b). This innovative GSA is featured with self-assembled polymeric nanosized vesicles entrapping three enzymes: glucose oxidase (GOx), α-amylase (AM) and glucoamylase (GA). GOx converts glucose into gluconic acid in the presence of oxygen. AM hydrolyses the α-amylose into disaccharides and trisaccharides, which further converts to glucose by GA (N. Gurung et al. Process Biochemistry 2003, 38, 1599; L. Kandra, Journal of Molecular Structure: THEOCHEM 2003, 666-667, 487).

Once subjected to the elevated BGLs, the GSA comprised of hypoxia-sensitive materials quickly disassociates to release the encapsulated enzymes in response to the rapid glucose oxidation by GOx and oxygen consumption (J. Yu et al. Proceedings of the National Academy of Sciences 2015, 112, 8260; O. Veiseh et al. Nature 2015, 524, 39):

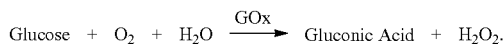

The released enzymes subsequently hydrolyze α-amylose (S. Peat, et al. Nature 1953, 172, 158; J. F. Robyt, D. French, Archives of Biochemistry and Biophysics 1967, 122, 8; W. J. Whelan et al. Nature 1952, 170, 748) embedded in the MN matrix, generating a local glucose-concentrated site. The "amplified" glucose effectively diffuses into the externally positioned β-cell capsules, promoting secretion and diffusion of insulin into the vascular and lymph capillary networks (A. J. Harvey et al. Pharmaceutical Research 2010, 28, 107). Using streptozotocin (STZ)-induced type 1 diabetic mouse as an animal model, it was demonstrated that the GRS consisting of ~$10^7$ β-cells quickly responded to a hyperglycemic state, declined and maintained BGLs at a reduced level for up to 10 hours. This cellular-synthetic hybrid glucose-responsive device with a physiological-signal amplifier modality presents a useful alternative to pancreatic β-cells implantation for tight regulation of BGLs.

Figure 2A:
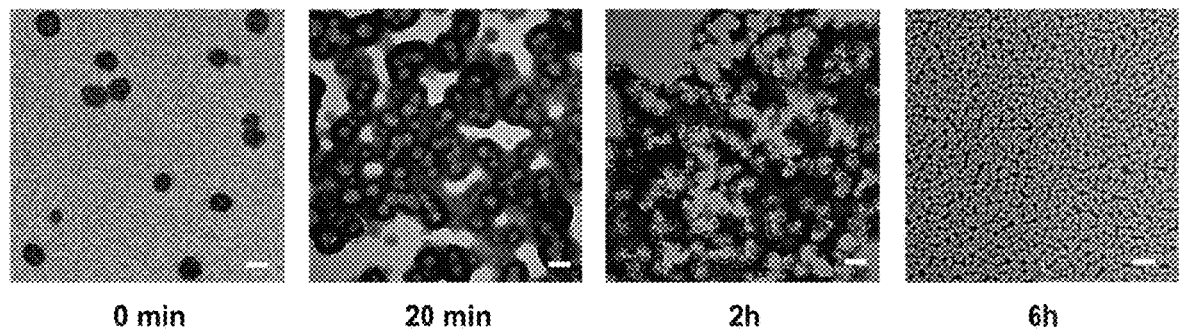
FIGS. 2A-F show a characterization of a glucose signal amplifier (GSA).
Figure 2B:
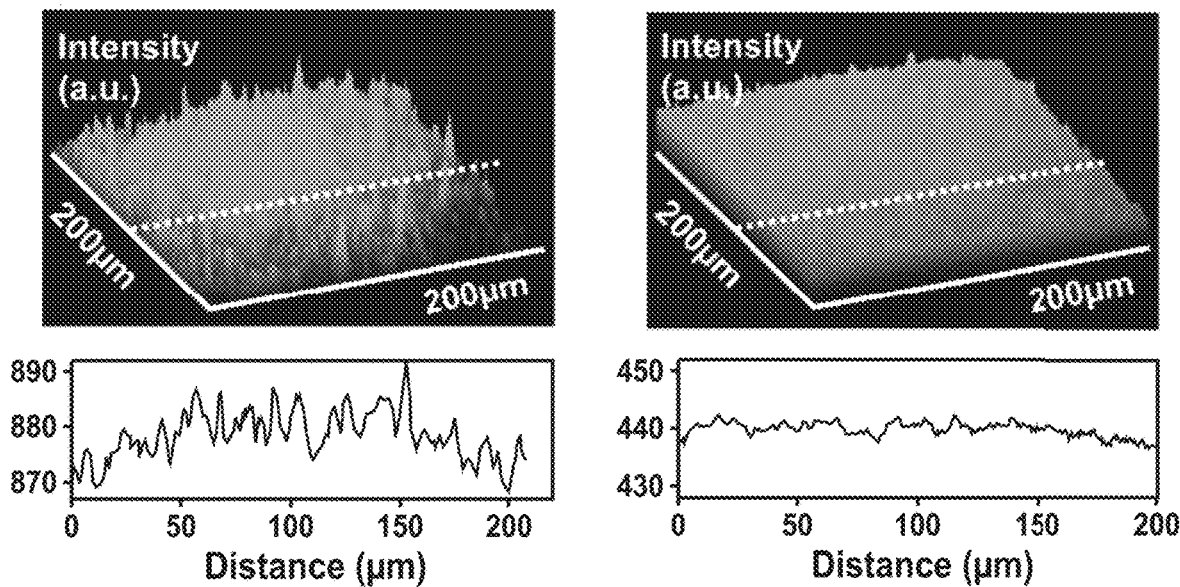
Figure 5:
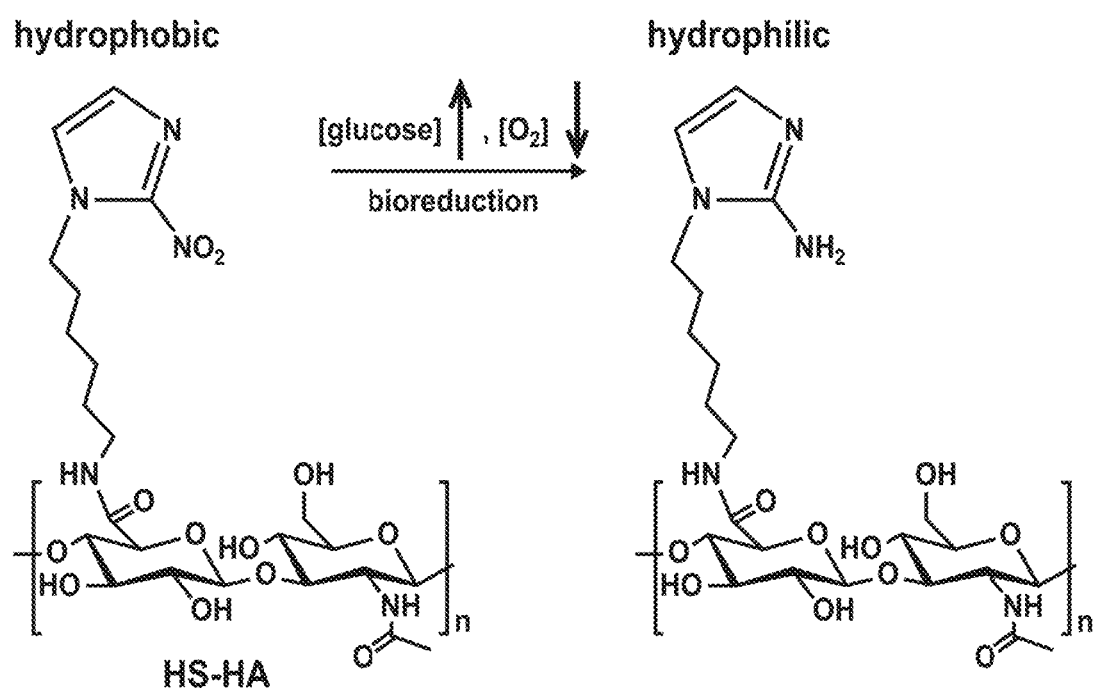
FIG. 5 shows a glucose-responsive mechanism of hypoxia-sensitive hyaluronic acid (HS-HA).

GSA was prepared by the solvent dialysis method for encapsulating three enzymes (J. E. Chung et al. Nature Nanotechnology 2014, 9, 907; H. Yu et al. Nature Communications 2014, 5). Briefly, amine-functionalized 2-nitroimidazole (NI) groups were covalently conjugated to the HA via an amide bond. The hypoxia-sensitive HA (HS-HA) functionalized with hydrophobic NI groups readily self-assembled into GSAs in the aqueous solution containing GOx, α-amylase and amyloglucosidase (FIG. 5). Under a hypoxic condition, the hydrophobic NI groups were reduced to hydrophilic 2-aminoimidazoles via a single-electron reaction with NADPH catalyzed by nitroreductases (Y. Seki et al. Journal of biochemistry 1970, 67, 389). The reduced product with amine groups was water-soluble, which facilitated the disassembly of GSA (J. Yu et al. Proceedings of the National Academy of Sciences 2015, 112, 8260; R. J. Hickey et al. Journal of the American Chemical Society 2011, 133, 1517). The transmission electron microscopy (TEM) image (FIG. 2a) showed that the GSA had a spherical shape with a monodisperse size. The average hydrodynamic size of GSA measured by dynamic light scattering (DLS) was 340 nm (FIG. 2c), which was consistent with the TEM images. The zeta-potential of GSA was determined as −45.7±2.4 mV due to the residual carboxyl of HA. The fluorescence image of GSA with fluorescein isothiocyanate (FITC)-labeled GA and AM further verified successful co-encapsulation of the enzymes (FIG. 2b). The loading capacity of GSA based on all the enzymes was determined as 7.4±0.5 wt % and loading efficiency as 16.1±1.0 wt %. The GSA was stable when incubated at 4° C. and no noticeable turbidity change was observed over two weeks.

Figure 2C:
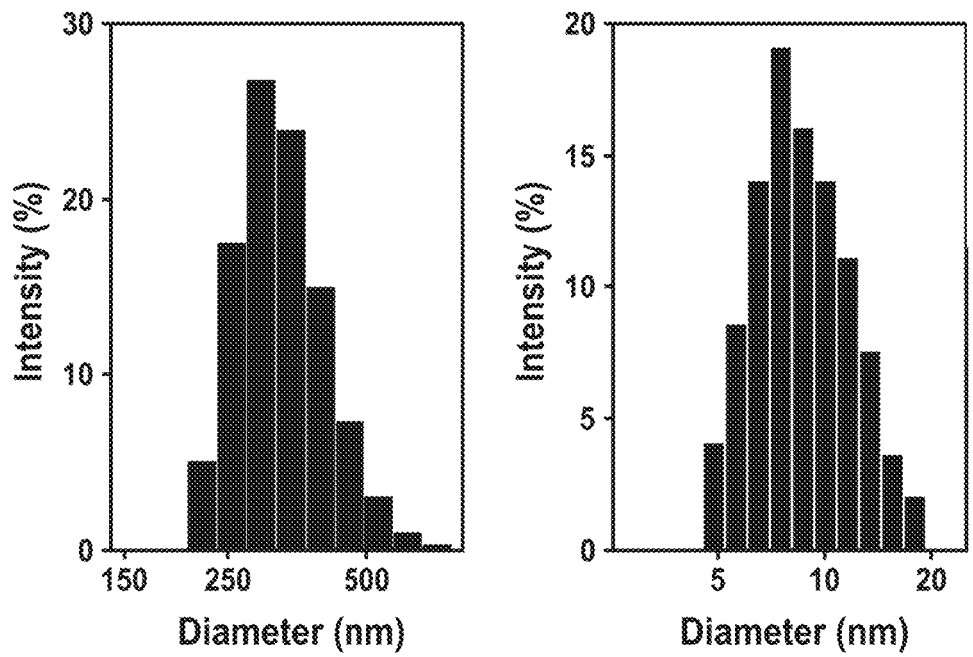
Figure 2D:
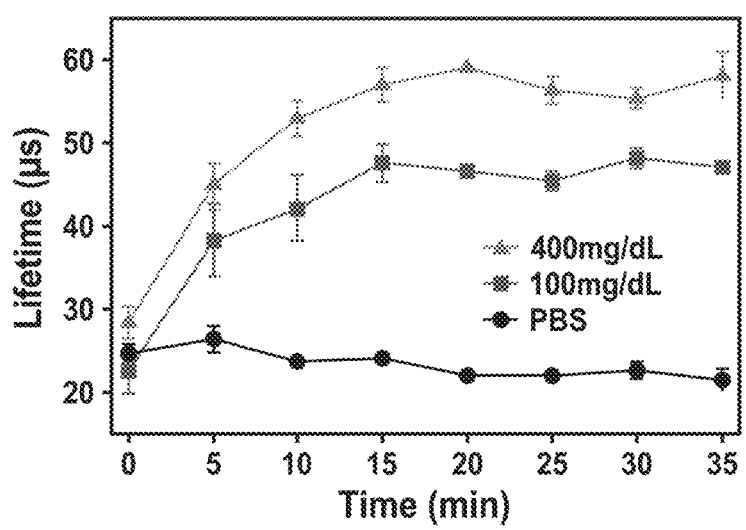
Figure 2E:
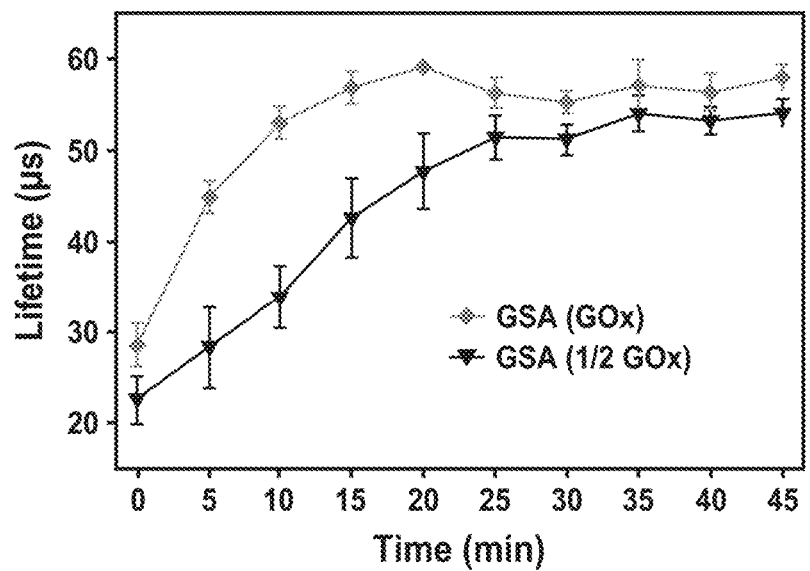
Figure 2F:
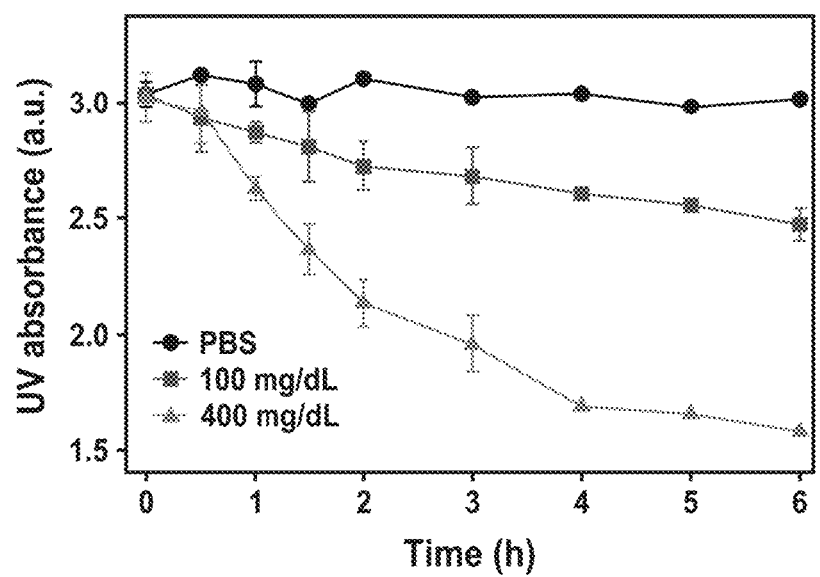
Figure 6:
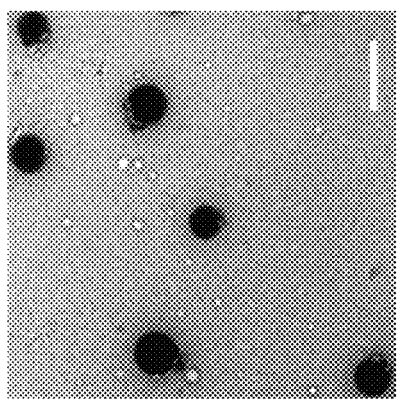
FIG. 6 shows the TEM images and DLS measurements of GSA after incubation with (from left to right) PBS buffer at 4° C., PBS buffer at 37° C. and PBS buffer containing a control level of glucose concentration (100 mg/dL) at 37° C. for 6 hours, respectively.
Figure 6:
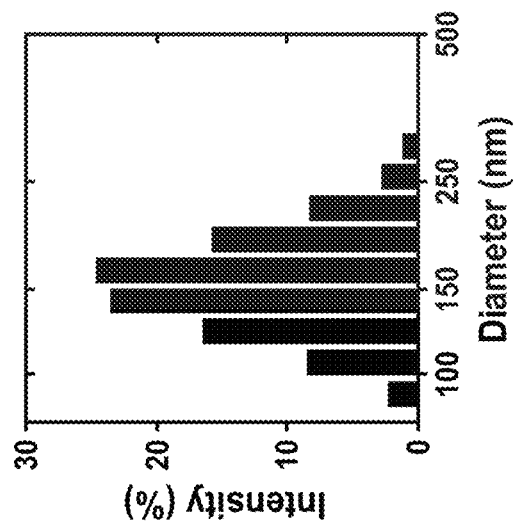
Figure 6:
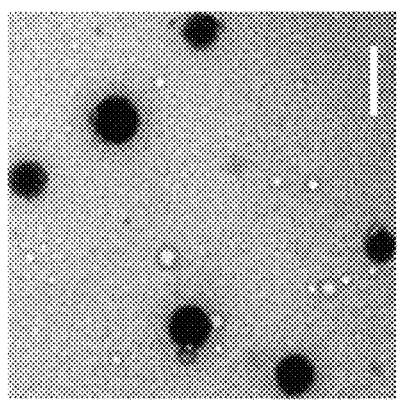
Figure 6:
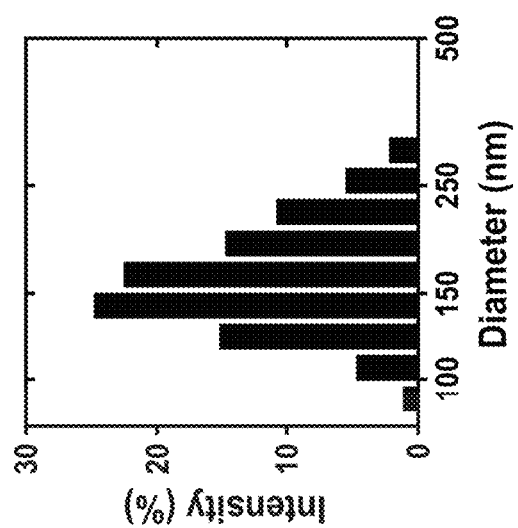
Figure 6:
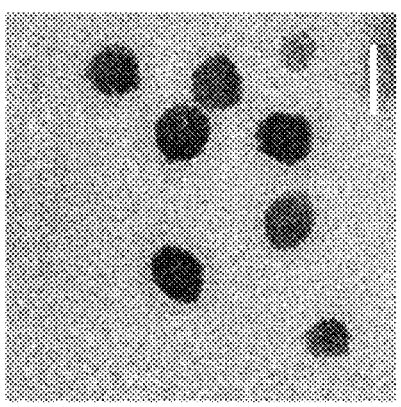
Figure 6:
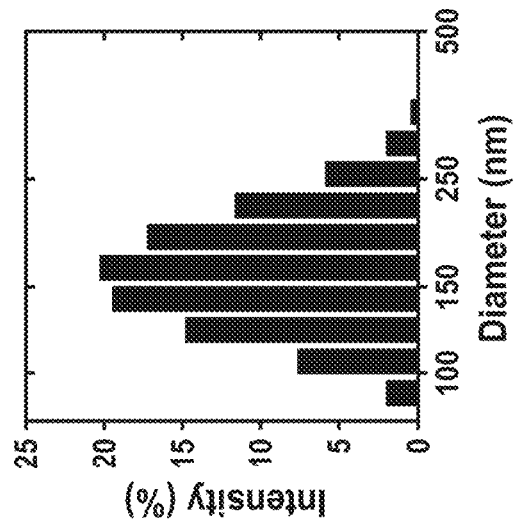

To assess the glucose-responsive capability of GSA in vitro, the vesicles were examined in 1×PBS buffer solutions with various glucose concentrations, including a typical hyperglycemic level (400 mg/dL), a normoglycemia level (100 mg/dL), and a control level (0 mg/dL). The hyperglycemia level generated a relatively lower oxygen environment in the GSA compared to the other two control groups, which was verified by an oxygen-sensitive phosphorescent molecular probe (FIG. 2d). The oxygen level inside the GSA gradually reduced over time and reached equilibrium within 20 min. The oxygen consumption kinetics could be further modulated by altering the amount of GOx loaded into the vesicle, which showed a clearly delayed hypoxic effect with a half dose of GOx (FIG. 2e). With the decline of oxygen level, the NI groups were effectively reduced by NADPH added into the solution. Correspondingly, the characteristic peak of NI at 330 nm in UV-Vis spectra decreased rapidly, which substantiated this bio-reduction reaction (FIG. 2f). Due to the generation of water-soluble pendant groups on HS-HA, the GSA began to dissociate and subsequently release the encapsulated enzymes. As shown in TEM images, the GSA in 400 mg/dL glucose solution experienced gradual morphology changes from 20 min to 6 h (FIG. 2a), which was consistent with the remarkable decline in the average hydrodynamic size, indicated by DLS (FIG. 2c). In contrast, GSA incubated with no glucose or 100 mg/dL glucose displayed stable hydrodynamic size and no noticeable morphology change (FIG. 6). Furthermore, the release of encapsulated FITC-labeled enzymes from the dissociated vesicles was visualized by fluorescence microscopy. The fluorescence signal intensity was significantly decreased and presented homogeneous distribution after 2 hours, suggesting that the enzymes escaped from the dissociated GSA and evenly dispersed in the solution (FIG. 2b).

Figure 3A:
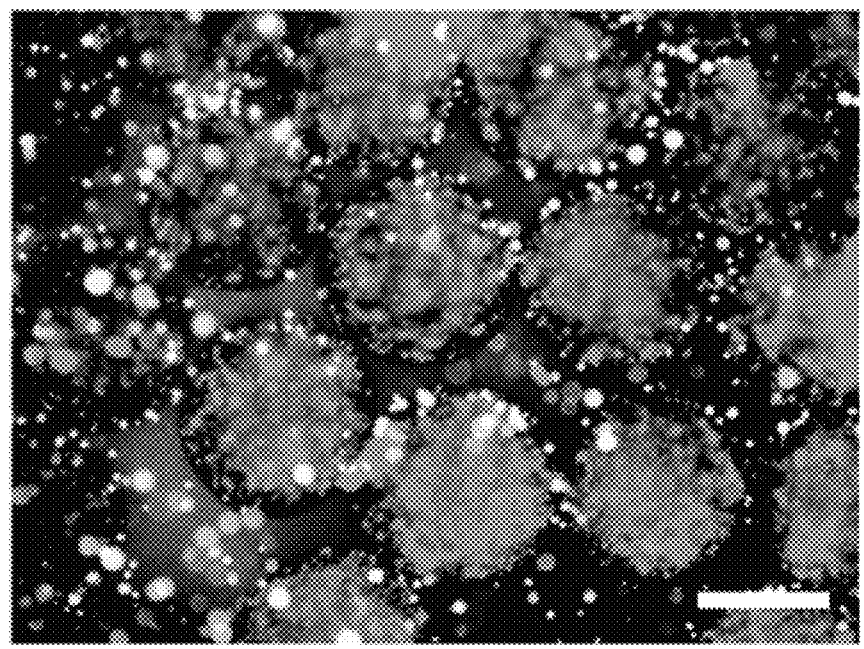
FIGS. 3A-I show in vitro glucose-responsive studies of GSA and characterization of the MN patch and L-S GRS.

The enzyme release kinetics in response to the glucose level changes were next examined. No significant amount of released enzymes from GSA was detected within 24 h of incubation at a normal glucose level (100 mg/dL) and a control level (0 mg/dL) (FIG. 3a). In sharp contrast, a rapid enzyme release rate was achieved from the GSA in the first 2 hours at a hyperglycemic environment (400 mg/dL). This was attributed to the faster reduction of NI groups, which was induced by the hypoxic condition upon glucose oxidation.

Figure 3B:
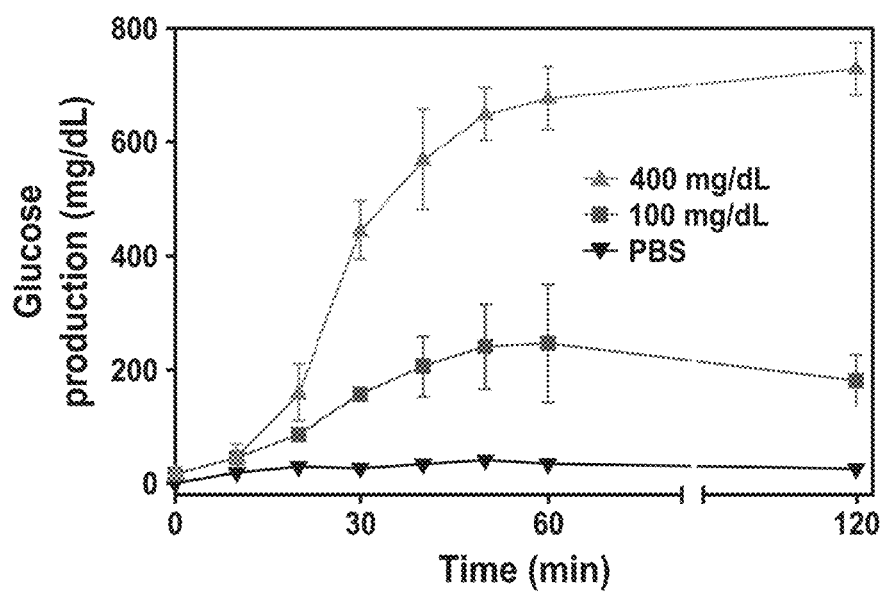
Figure 7:
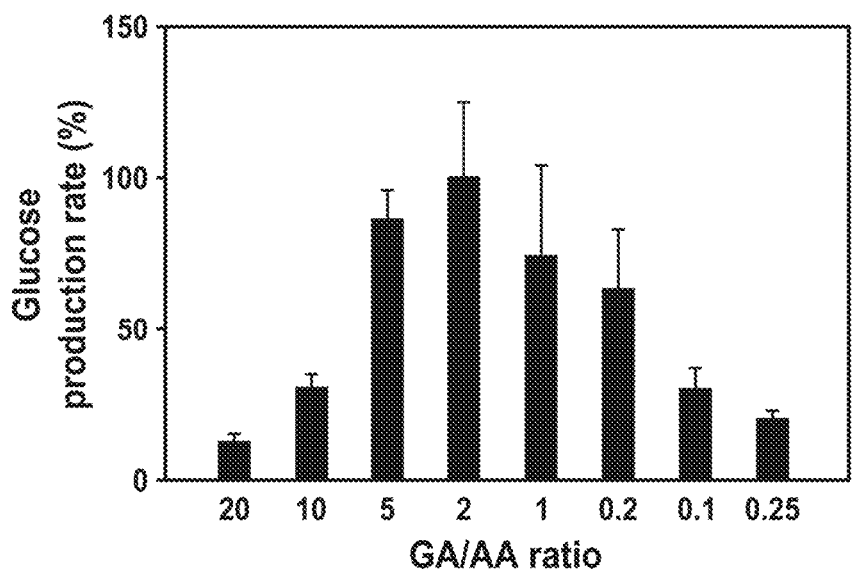
FIG. 7 shows the normalized glucose production rate at different enzymes weight ratio between GA to AA. Error bars indicate s.d. (n=3).
Figure 8:
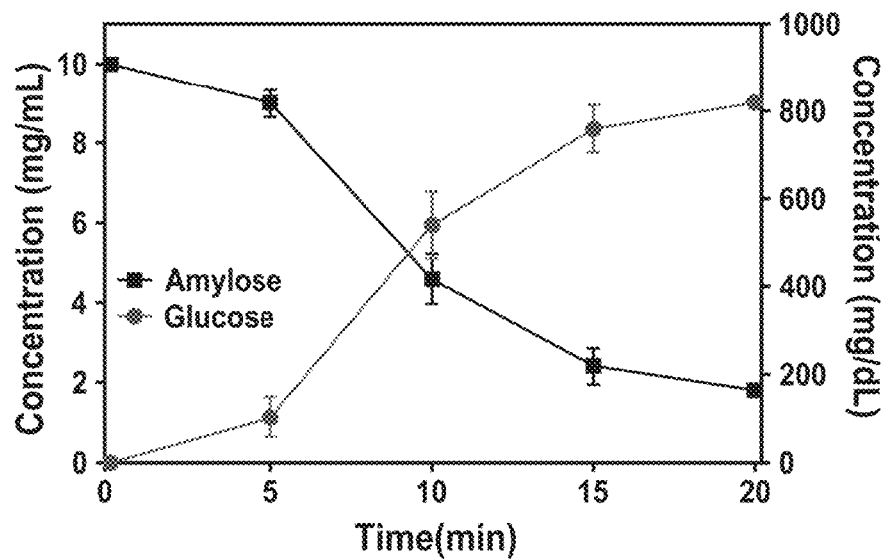
FIG. 8 shows conversion of α-amylose to glucose in 10 mg/mL α-amylose solution with 3 mg/mL AA and 6 mg/mL GA. Error bars indicate s.d. (n=3).
Figure 9A:
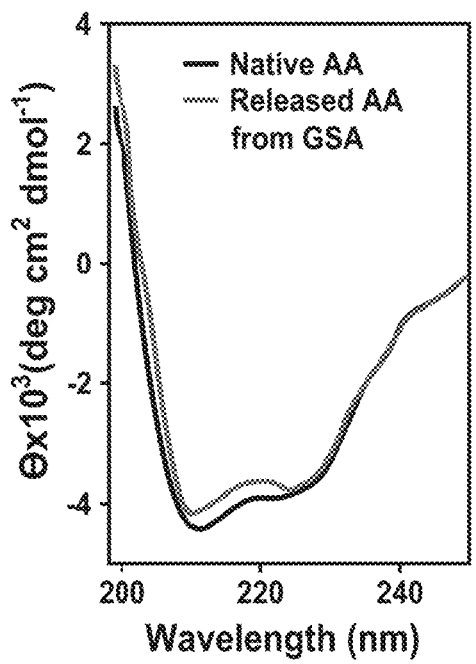
FIGS. 9A-B show CD spectra of (a) AA and (b) GA in the native states and the ones released from the GSA incubated in solutions with 400 mg/dL glucose at 37° C. for 6 hours.
Figure 9B:
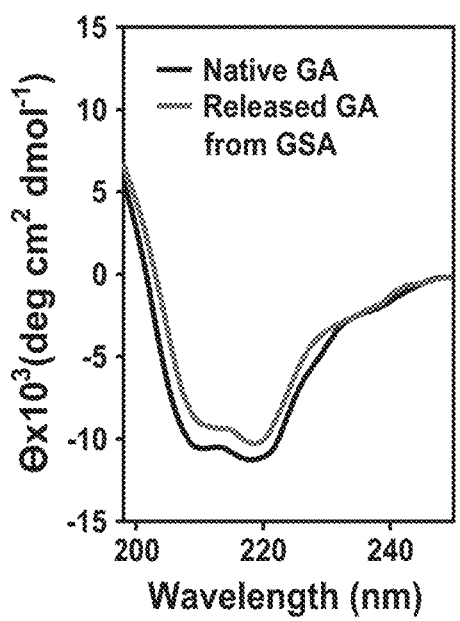

Afterwards, the conversion from α-amylose to glucose catalyzed by the released enzymes from GSA was further investigated. The encapsulation ratio of AA to GA was pre-optimized as 1:2 by analyzing their enzymatic hydrolysis capability of α-amylose, indicated by the glucose production rate (FIG. 7). When AA and GA were utilized to saccharify 10 mg/mL α-amylose solution sequentially, the glucose production was readily increased to 816±26 mg/dL, yielding an 81.6% conversion rate of α-amylose (FIG. 8). The circulation dichroism (CD) spectra confirmed that the released enzymes GA and AA from GSA maintained their secondary conformational structures (FIG. 9). Meanwhile, when the GSA was incubated in α-amylose solutions with various glucose concentrations, a significantly faster glucose production was achieved when incubated with 400 mg/dL glucose compared to the one with 100 mg/dL glucose (FIG. 3b). It indicated that the enzymatic hydrolysis of α-amylose was activated by the gradual release of enzymes associated with the disassembly of GSA. Taken together, once "sensing" the elevated glucose level, the GSA could be activated to release the enzymes, which promoted the α-amylose-to-glucose conversion to amplify the glucose signal for downstream action.

Figure 3C:
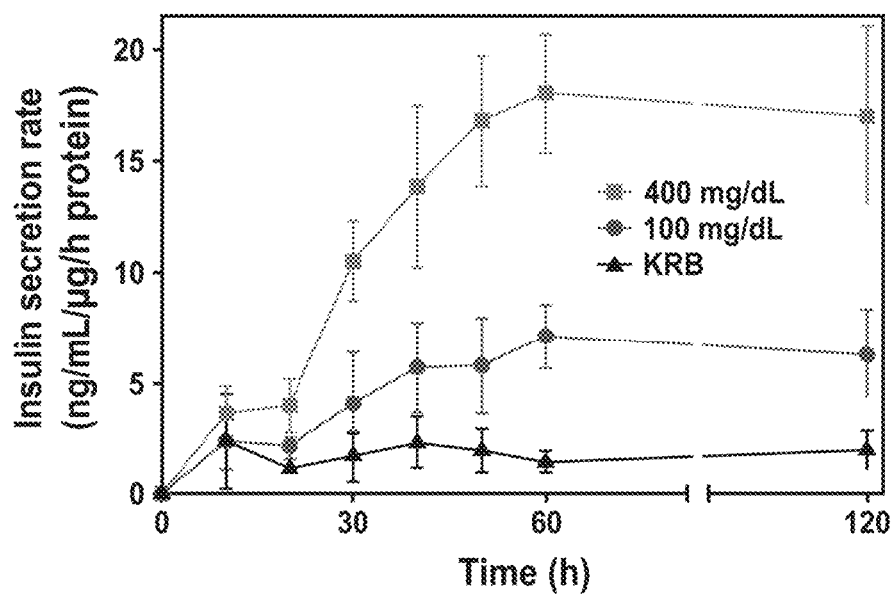
Figure 3D:
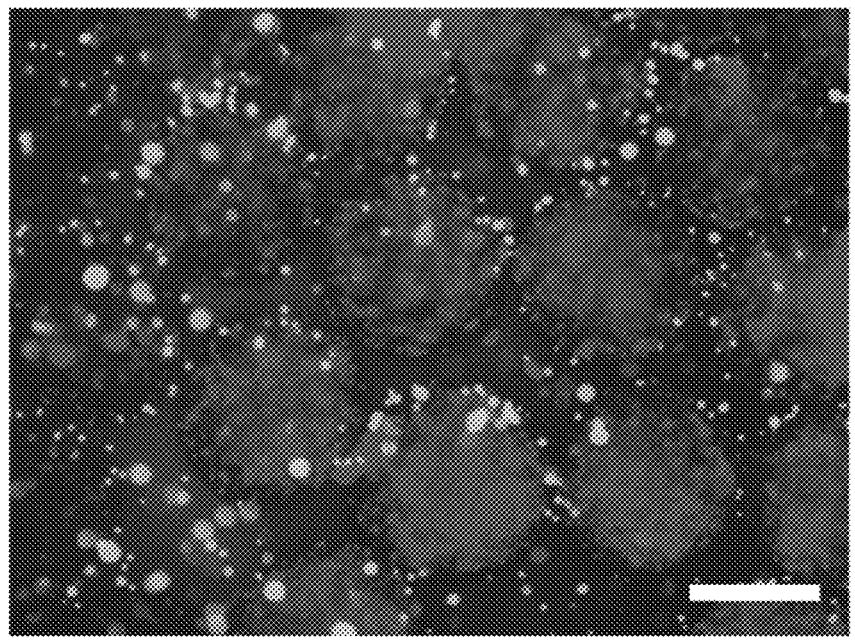
Figure 3E:
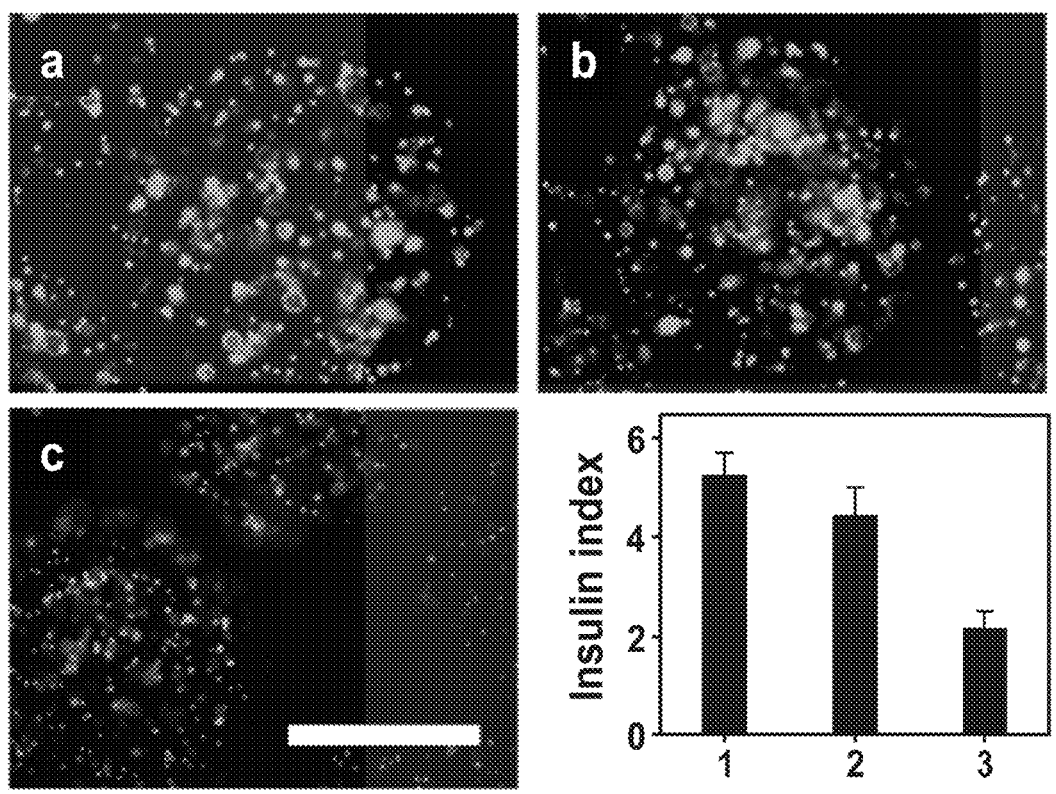
Figure 10:
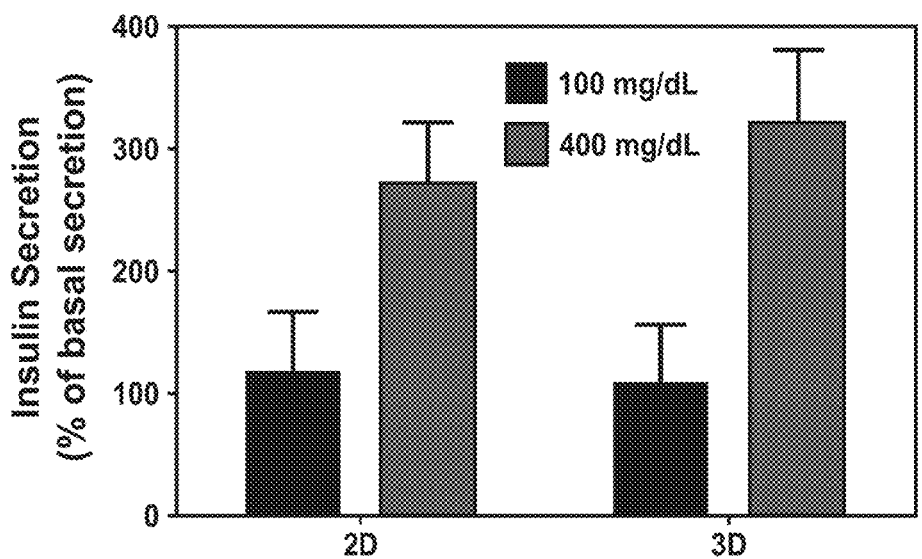
FIG. 10 shows glucose stimulated insulin secretion of the cells cultured on a 2D tissue culture plate and the cells encapsulated in 3D capsules 30 hours post encapsulation. The amount of insulin secretion in 400 mg/dL glucose KRB was normalized to insulin secretion in 100 mg/dL glucose KRB. Error bars indicate s.d. (n=3).

The use of MN patches for the delivery of insulin from pancreatic β-cell capsules was further investigated. To create the "live" glucose-responsive component of the L-S GRS, the mouse islets β-cell lines were encapsulated in alginate microgels with RGD (C. C. Lin et al. Proceedings of the National Academy of Sciences 2011, 108, 6380.) and type IV collagen (L. M. Weber et al. Biomaterials 2007, 28, 3004.) at $2 \times 10^6$ cell/mL packing density to provide a benign environment with biomimetic cell-ECM adhesive interactions. Successful encapsulation was visualized by fluorescence microscopy with the concentrated cells and homogenous distribution of the secreted insulin surrounding the capsules (FIG. 3d). The size of the obtained capsule was 735±27 μm. The glucose stimulated insulin secretion (GSIS) analysis and live-dead assay were performed after day 1 to day 3 to validate that the encapsulated β-cells maintained their viability and functionality (FIG. 3e) C. C. Lin et al. Proceedings of the National Academy of Sciences 2011, 108, 6380.). The results indicated that the encapsulated β-cells could survive for a relatively long period of time and maintain normal glucose-responsive insulin secretion capability when compared their insulin secretion index with cells cultured on a 2D tissue culture plate (FIG. 10).

Figure 11:
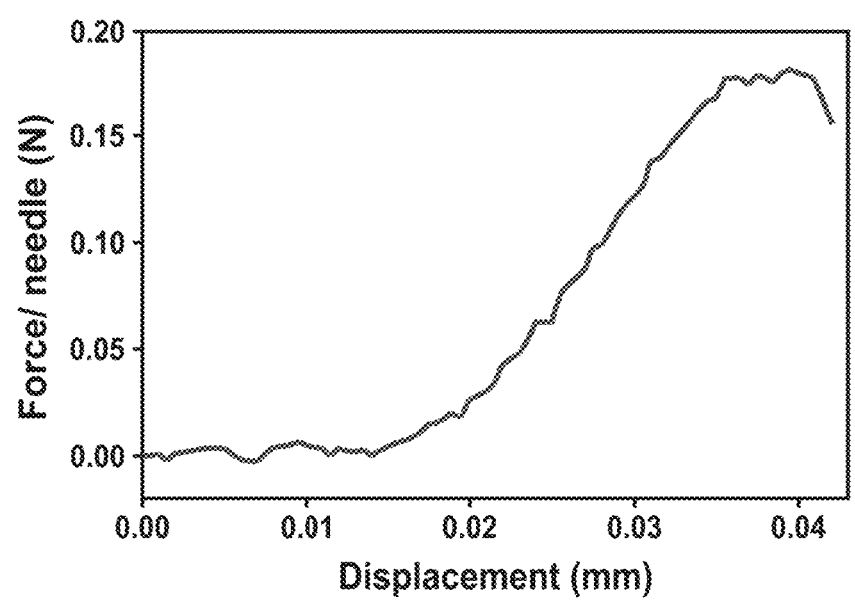
FIG. 11 shows the mechanical behavior of the GSA-loaded crosslinked MN. (n=5).

Meanwhile, the MN patch was fabricated using a micromolding approach. The resulting MN device had 400 pyramid needles in a 10-mm² patch, and each needle had a side length of 400 μm at the base, a side length of 5 μm at the tip, and a height of 800 μm (FIG. 3g, 3h). The needle was designed to have a triple-layered structure consisting of GSA, α-amylose and crosslinked hyaluronic acid matrix using alternating deposition. The mechanical strength of MN was determined as 0.18 N/needle, which was sufficient for skin penetration without breaking (FIG. 11) (S. P. Sullivan et al. Nature Medicine 2010, 16, 915). A fluorescence view depicted the representative integration of MN patch with the pancreatic β-cells capsules (FIG. 3i). GSAs were well distributed in tip region of the MNs and the cell-embedded capsules were positioned on the back of the MN patch.

Figure 3F:
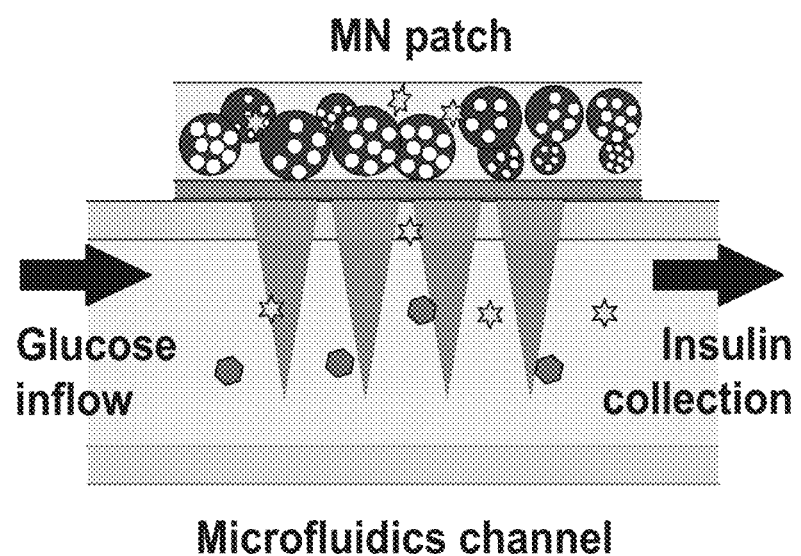
Figure 3G:
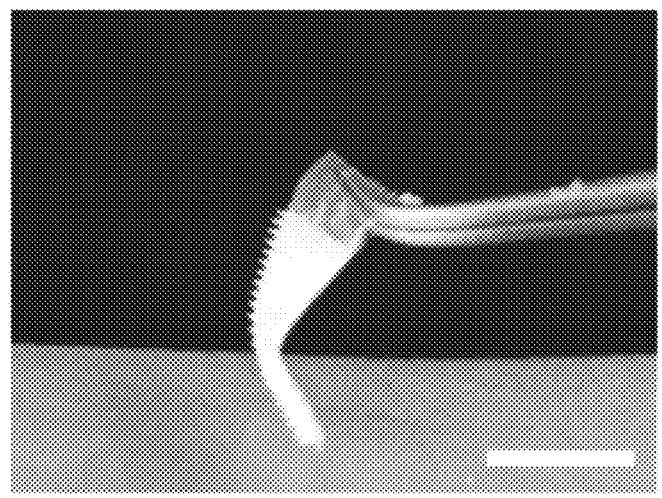
Figure 3H:
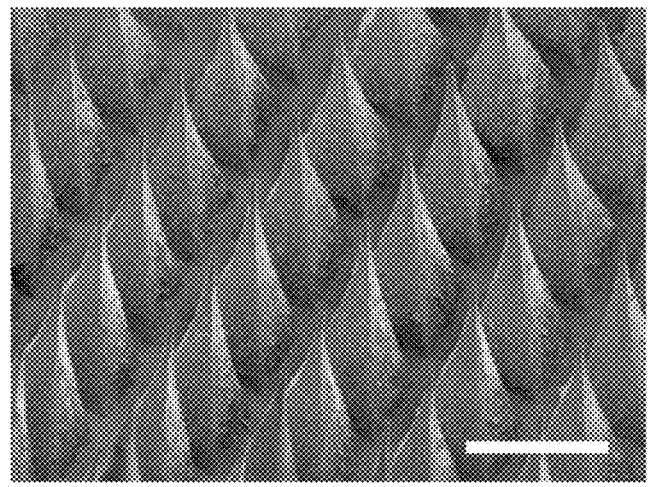
Figure 3I:
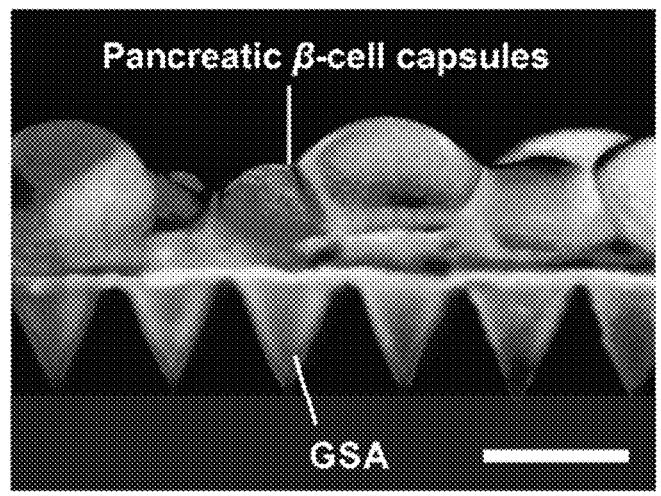

The GSIS of L-S GRS was examined through the microfluidics (FIG. 3f). The needles on the patch were incubated in an open microfluidic channel with continuous infusion of the Krebs-Ringer buffer (KRB) with a hyperglycemic level (400 mg/dL) and a normoglycemia level (100 mg/dL) respectively. The GSIS with the high glucose level infusion displayed a 3-fold increase compared to the low glucose one (FIG. 3c). This was attributed to the hyperglycemic flow, which quickly promoted the dissociation of GSA; and the subsequent hydrolysis of α-amylose led to an amplified, sufficient glucose level signal for triggering the secretion of insulin from the β-cells capsules.

Figure 4A:
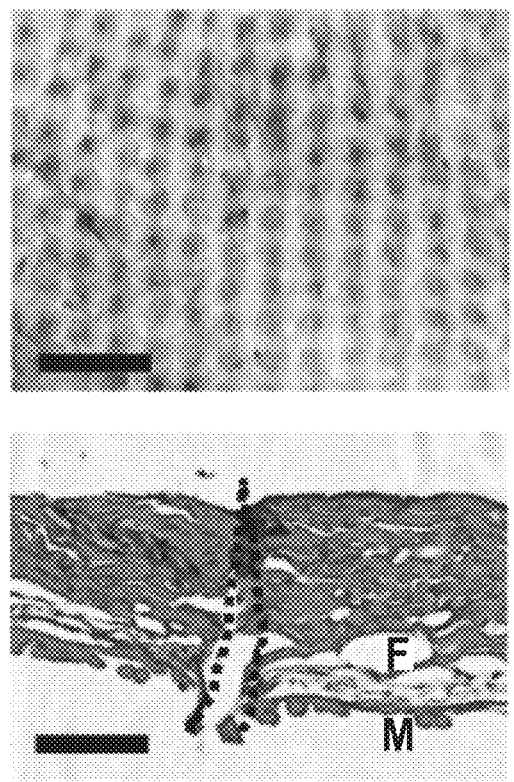
FIGS. 4A-F show in vivo studies of L-S GRS for type 1 diabetes treatment.

To investigate the in vivo efficacy of the glucose-responsive MN device, STZ-induced type 1 diabetic mice were subjected to transcutaneous administration of a variety of MNs samples: empty MNs without GRS (w/o GRS), MNs integrated with only L-GRS (L-GRS), MNs integrated with only S-GRS (S-GRS), MNs integrated with L-S-GRS (L-S GRS), MNs integrated with L-S-GRS but without GOx in S-GRS (L-S GRS (w/o GOx)), and MNs integrated with L-S-GRS but without α-amylose in S-GRS (L-S GRS (w/o AM)). Each MN patch was administered by a homemade applicator with 5N/patch to ensure the uniform penetration and was immobilized on the skin by topical skin adhesive. The excised skin tissue clearly showed the visible sites of needle insertion (FIG. 4a, top) and the hematoxylin and eosin (H&E)-stained cross-section image indicated that MNs could penetrate to a depth of approximately 200 μm to the epidermis (FIG. 4a, bottom), which allowed the GSA to be exposed to interstitial fluid in real-time (S. P. Sullivan et al. Nature Medicine 2010, 16, 915).

Figure 4B:
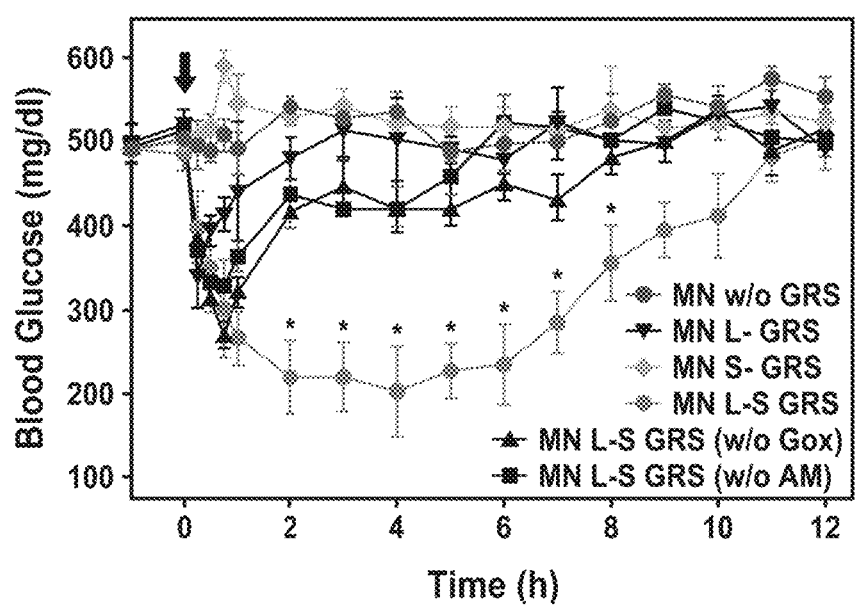
Figure 12:
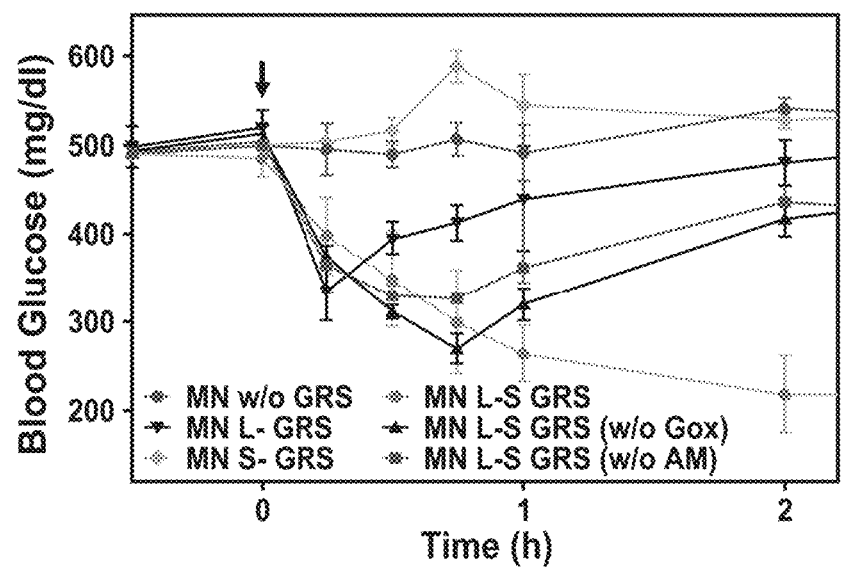
FIG. 12 shows BGLs of treated STZ-induced diabetic mice, which were continuously monitored in the first two hours after administration of MN w/o GRS, MN L-GRS, MN S-GRS, MN L-S-GRS, MN L-S GRS (w/o GOx) and MN L-S GRS (w/o AM). The black arrows indicate the administration points. Error bars indicate s.d. (n=5). *$P<0.05$ for diabetic mice treated with MN L-S GRS administration compared to the healthy mice.

The BGLs of treated mice in each group were monitored over time. As shown in FIG. 4b, the BGLs in mice treated with MN patch integrated with L-S GRS quickly declined to nearly 200 mg/dL within two hours and maintained in a significantly reduced level for 6 h without peaks of hyperglycemic or hypoglycemic states. In contrast, without the complete S-GRS (L-GRS group) or just lacking the responsive element-GOx (L-S GRS (w/o GOx) group) or amplifying element-AM (L-S GRS (w/o AM) group), the BGLs only decreased in the first hour, which could be explained by the diffusion of residual amounts of insulin detained in the hydrogel. Afterwards, the insulin secretion of β-cells maintained at the basal level and the BGLs of mice reverted to the hyperglycemic state. In the absence of β-cell capsules, the groups treated with MNs integrated with only S-GRS (S-GRS) or empty MN (w/o GRS) groups displayed no noticeable decline in BGLs as expected. The temporarily elevated BGLs in S-GRS group could be attributed to the induced hydrolysis of α-amylose and the host glucose clearance (FIG. 12).

Figure 4C:
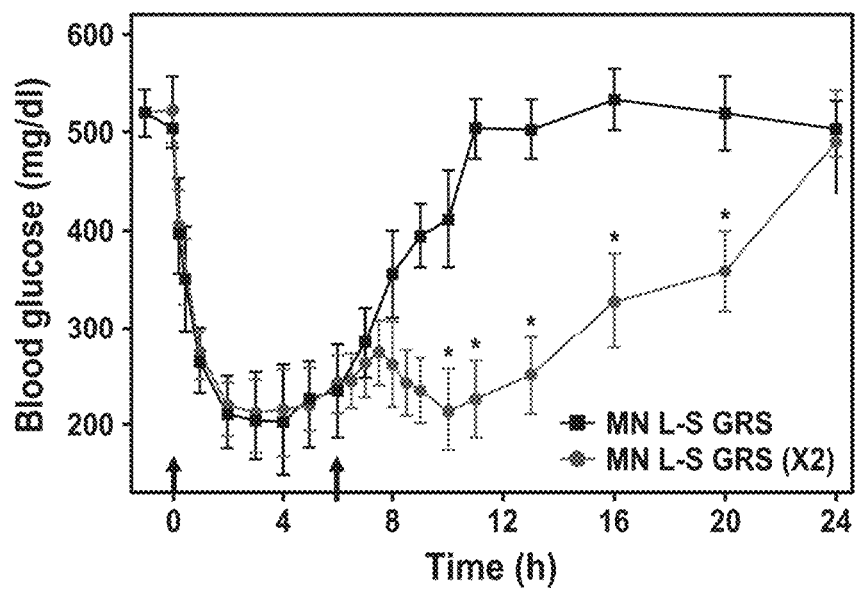
Figure 4D:
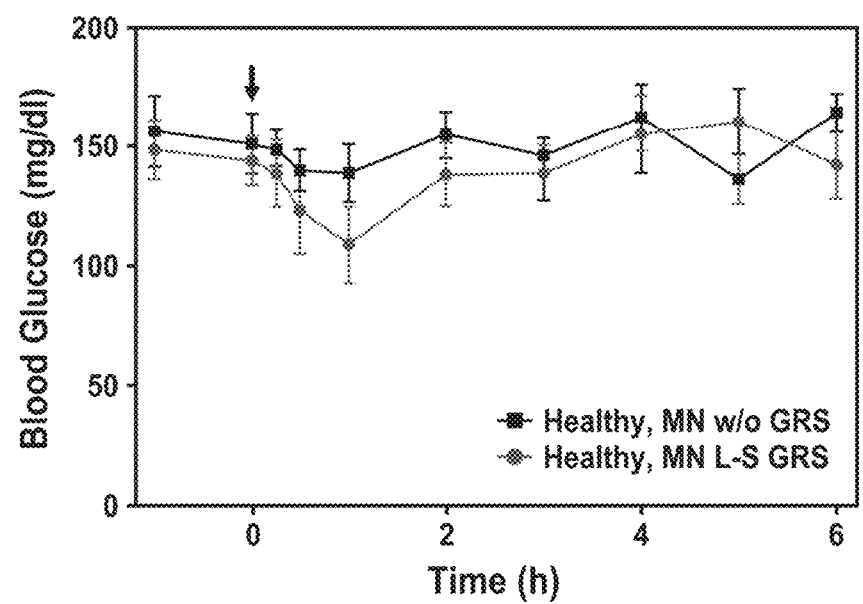
Figure 4E:
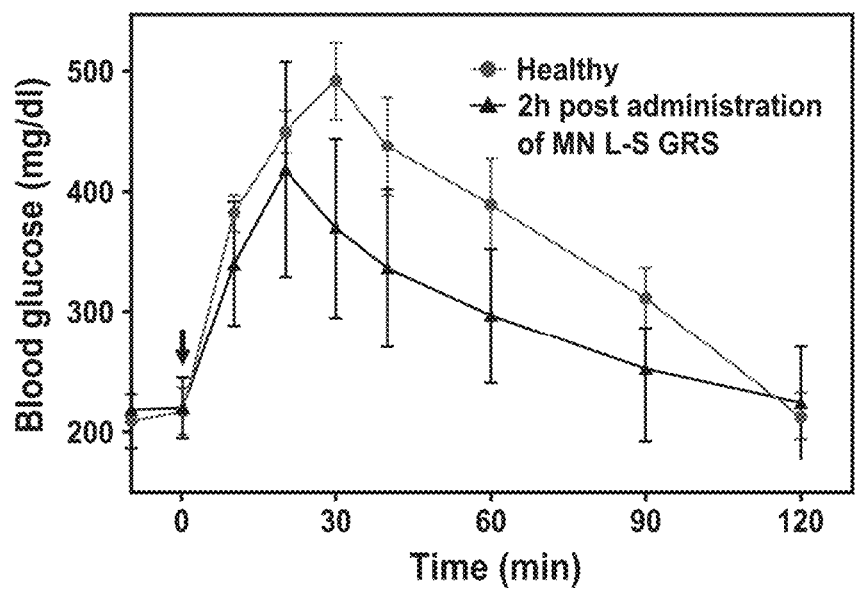
Figure 4F:
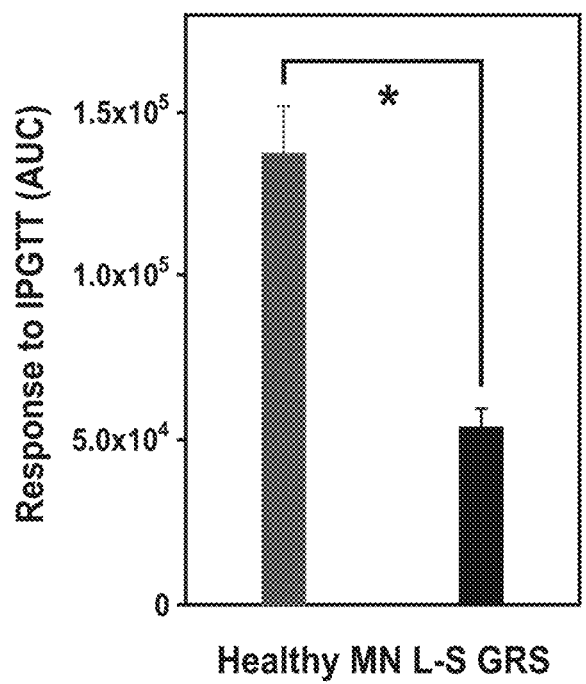

To assess whether the MN patch could modulate the BGLs without causing potential risks of hypoglycemia, a group of STZ-induced mice were subjected to the MN patch replacement administration. The second MN patch treatment 6 hour post the first administration did not secrete excess insulin in absence of hyperglycemia trigger, which could avoid the hypoglycemia risk. Moreover, the additional MN patch was able to prolong the treatment efficiency in response to the elevated BGLs compared to the control (FIG. 4c). The study on the healthy mice treated with MN patches integrated with L-S GRS and empty MN as control demonstrated that the device did not cause hypoglycemia (FIG. 4d). Insignificant insulin release from the L-S GRS still maintained the BGLs of mice in a normal range. A glucose tolerance test demonstrated the tight glucose regulation capability on diabetic mice (J. Yu et al. Proceedings of the National Academy of Sciences 2015, 112, 8260; D. H.-C. Chou et al. Proceedings of the National Academy of Sciences 2015, 112, 2401). At 2 hours after administration of the L-S GRS, the diabetic mice were treated with an intraperitoneal (i.p.) glucose injection. BGLs of diabetic mice showed a 100 mg/dL increase and rapid decline to initial BGLs within 60 minutes (FIG. 4e). The area under the curve between 0 and 120 minutes was calculated to indicate the MN maintenance of glucose homeostasis. Significant difference was observed between MN group and the control group 2 h post glucose challenge (FIG. 4f).

Figure 13:
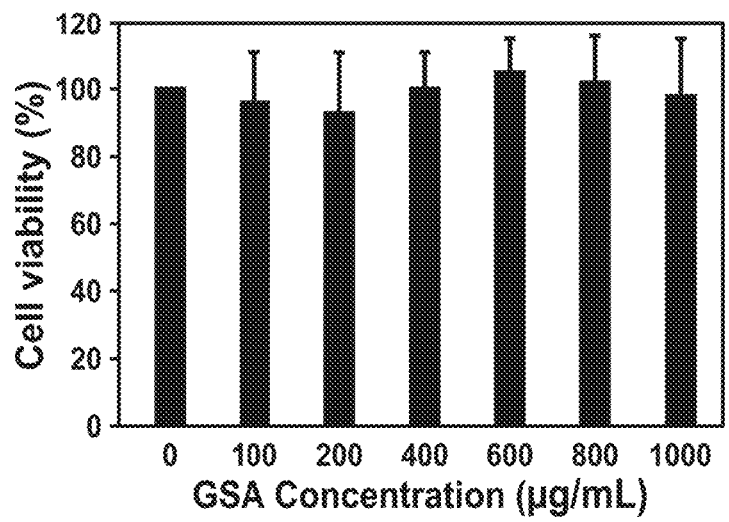
FIG. 13 shows a cytotoxicity study of GSA after 24-hour incubation with MIN6 cells. Error bars indicate s.d. (n=6).
Figure 14A:
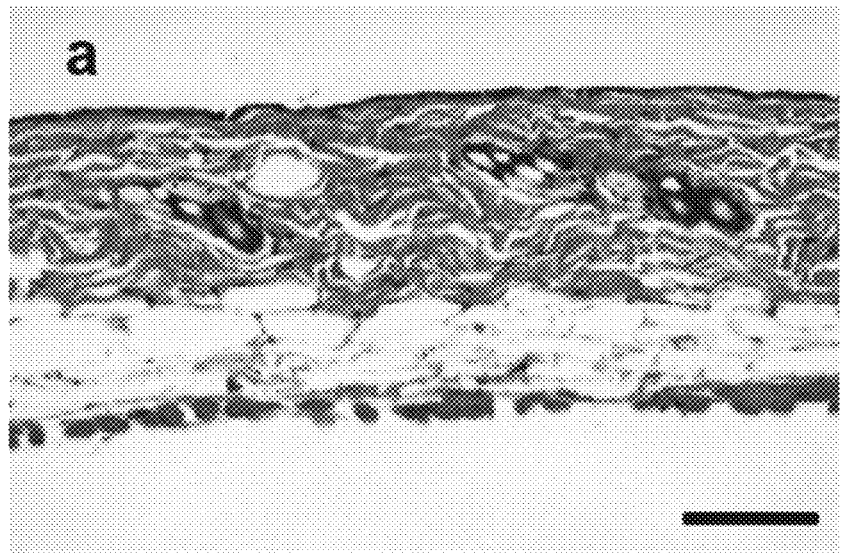
FIG. 14A-B shows H&E-stained skin cross-section of surrounding tissues with administration of PBS (a) or a MN patch (b) 2 days post-treatment. Those skin samples were at a distance of 5 mm from the MN injection site. Scale bar is 200 μm.
Figure 14B:
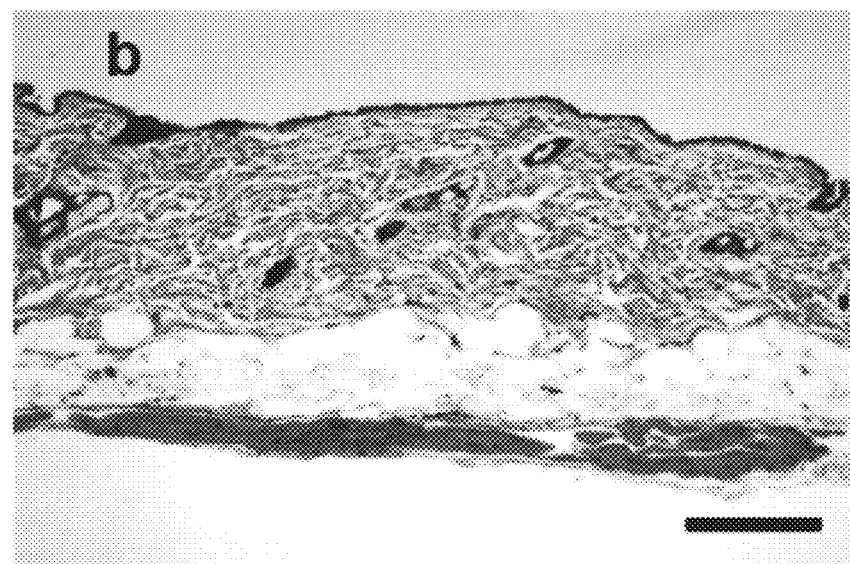

To assess the biocompatibility of the GSA-loaded MN patch, the cytotoxicity of dissolved microneedles toward β-cells was evaluated by MTT assay (FIG. 13). The MNs and corresponding dissolved products did not show significant decrease of cell viability with the studied concentrations. The skin treated by the MN patch could rapidly recover within 8 hours after MN removal and the H&E stained skin section of the injection site presented no obvious inflammation (FIG. 14) (W. Yuan et al. Drug Design, Development and Therapy 2013, 945).

Currently, the biocompatibility and safety issues significantly hamper the clinical applications of pancreatic islet cells transplantation (O. Veiseh et a. Nature Reviews Drug Discovery 2014, 14, 45; S. Mitragotri et al. ACS Nano 2015, 9, 6644; K. M. Bratlie et al. Advanced Healthcare Materials 2012, 1, 267). Instead of utilizing traditional administration methods and relying on an invasive procedure, a microneedle patch-based strategy was developed to control the insulin secretion from externally positioned pancreatic β-cells, triggered by the internal hyperglycemic state. Importantly, for the first time, a synthetic amplifier was incorporated to quickly amplify the physiological signal, in this case "glucose level", for effective transport of the signal and sufficient stimulation of insulin secretion from the β-cells. The results of serial treatments in vivo showed the potency of the MN patches in tight glucose regulation for a prolonged period. This method circumvents the challenging issues for pancreatic cells therapy associated with immune response and long-term efficacy. This effective administration period can be further extended by optimizing the density and viability of cells as well as the physicochemical properties of matrix material for transporting glucose and insulin. In one example, freshly-prepared patches with pig islets or stem cell-differentiated human pancreatic cells can be delivered to patients every 1, 2, 3, 4, 5, 6, 7, or more days for ease of administration. Disclosed are synthetic amplifiers for enhancing efficacy of physiological signal-responsive drug delivery systems when the original bio-signal is insufficient for triggering responsiveness.

Methods Used in Example 1

Materials

All chemicals unless mentioned were purchased from Sigma-Aldrich. Sodium hyaluronic acid (HA, the molecular weight of 300 kDa) was purchased from Freda Biochem Co., Ltd. (Shandong, China), custom synthetic peptide (CGRGDS, MW 594.31) was purchased from Celtek Bioscience, LLC. (Franklin, Tenn.), anti-insulin antibody (ab181547) and goat anti-rabbit IgG H&L (FITC) (ab6717) were purchased from Abcam, skin affix surgical adhesive was purchased from Medline Industries, Inc.

Synthesis and Characterizations of Hypoxia-Sensitive Hyaluronic Acid (HS-HA)

Hypoxia-sensitive hyaluronic acid (HS-HA) was synthesized by chemically conjugating 6-(2-nitroimidazole) hexylamine through amide formation. First, 6-(2-nitroimidazole) hexylamine was synthesized to react with the carboxylic acids groups of HA. In brief, NI (0.15 g, 1.3 mmol) was dissolved in DMF, to which $K_2CO_3$ (0.28 g, 2.0 mmol) was added. Then 6-(Boc-amino) hexyl bromide (0.39 g, 1.4 mmol) was added dropwise into the solution and stirred at 80° C. for 4 hours. The solid impurities were separated from the reaction mixture through filtration and washed with methanol. The solid product was obtained from the residual solvent by evaporation, which was suspended in deionized (DI) water and then extracted with ethyl acetate. The organic layer was collected and concentrated with sodium sulfate. The product was re-dissolved in methanol on the ice. 5 mL of 1.25 M HCl in methanol was added to the solution and stirred for 24 h at room temperature (RT). Afterward, the solvent was removed using rotary evaporator to obtain the amine-functionalized NI. Second, 6-(2-nitroimidazole) hexylamine was conjugated to HA in the presence of 1-ethyl-3-(3-dimethylaminopropyl)carbodiimide (EDC) and N-hydroxysuccinimide (NHS). Briefly, 0.24 g of HA (molecular weight: ~300 kDa) was dissolved in water, to which EDC (0.56 g, 3.4 mmol) and NHS (0.39 g, 3.4 mmol) were added and stirred for 15 minutes at room temperature. Later 6-(2-nitroimidazole) hexylamine (0.18 g, 0.85 mmol) in DMF was added to the mixture and reacted at room temperature for 24 hours. The dialysis was performed thoroughly against a 1:1 mixture of DI water and methanol for 24 h and DI water for 48 hours. Then, HS-HA was obtained by lyophilization and characterized by $^1$H NMR (Varian Gemini 2300). The graft degree is determined as 20% by UV-Vis absorbance.

6-(2-nitroimidazole) hexylamine: $^1$H NMR (DMSO-$d_6$, 300 MHz, δ ppm): 1.30-1.78 (m, 8H, $NH_2CH_2(CH_2)_4$), 2.73 (s, 2H, $NH_2CH_2$), 4.38 (s, 2H, $NCH_2$), 7.19 (s, 1H), 7.87 (s, 1H).

HS-HA: $^1$H NMR ($D_2O$, 300 MHz, δ ppm): 1.88-2.40 (m, 8H, $NH_2CH_2(CH_2)_4$), 2.87-3.19 (m, 4H, $NH_2CH_2$, $NCH_2$), 7.19 (s, 1H), 7.48 (s, 1H).

Preparation and Characterization of Methacylated Hyaluronic Acid (m-HA)

Hyaluronic acid (HA) was modified with double bond by reacting with the methacrylic anhydride (MA). Two grams of HA was dissolved in 100 mL of distilled (DI) water in cold room overnight, followed by the dropwise addition of 1.6 mL of methacrylic anhydride (MA). The reaction solution was maintained between pH 8-9 by adding 5 N NaOH and continuously stirred at 4° C. for 24 hours. Subsequently, m-HA was precipitated in acetone, washed with ethanol 3 times and then dissolved in DI water. After dialysis against DI water for 48 hours, the purified m-HA was obtained with a yield of 87.5% by lyophilization and characterized by $^1$H NMR(Varian Gemini 2300). The degree of modification (DM) was calculated to be about 15% by comparing the ratio of the areas under the proton peaks at 5.74 and 6.17 ppm (methacrylate protons) to the peak at 1.99 ppm (N-acetyl glucosamine of HA) after performing a standard deconvolution algorithm to separate closely spaced peaks.

m-HA: $^1$H NMR ($D_2O$, 300 MHz, δ ppm): 1.85-1.96 (m, 3H, $CH_2$=$C(CH_3)CO$), 1.99 (s, 3H, $NHCOCH_3$), 5.74 (s, 1H, $CH^1H^2$=$C(CH_3)CO$), 6.17 (s, 1H, $CH^1CH^2$=$C(CH_3)CO$).

Rheological experiments of the m-HA hydrogel were conducted at 37° C. using a TA Instruments AR-2000 stress controlled rheometer with sandpaper covered parallel-plate (25 mm). The 2 wt % m-HA hydrogel in Dulbecco's Modified Eagle Medium (DMEM) were crosslinked by in situ photopolymerization with N,N'-methylenebisacrylamide (MBA 2%, w %) and photoinitiator (Irgacure 2959; 0.05%, wt %) via UV irradiation (wavelength: 365 nm, intensity: 9 W/cm$^2$) for 1 minute. Experiments were performed within the linear viscoelastic regime at 0.5 Pa geometries with a 2 mm gap. Measurements were performed at least thrice to ensure reproducibility within ±10%.

Preparation and Characterization of GSA

GSA was prepared by self-assembly in aqueous solution. Briefly, 20 mg of amphiphilic HS-HA was dissolved in water/methanol (2:1 vol/vol), followed by addition of 1 mg of GOx from *Aspergillus niger* (200 U/mg, 160 kDa/7 nm), 3 mg α-amylase from *Bacillus licheniformis* (500-1,500 U/mg, 51 kDa/2.43 nm) and 6 mg of amyloglucosidase from *Aspergillus niger* (≥300 U/mL, 75 kDa/3.35 nm). The mixture was stirred at 4° C. for 2 hours. Then, the methanol was removed by dialysis against deionized water for 1 day. The resulting GSA suspension was further filtered by a centrifugal filter (100 kDa molecular mass cutoff, Millipore) at pH 7.4 to remove the unloaded enzymes by centrifugation at 14,000×g for 10 min. The final GSA suspension was stored at 4° C. for further study. For the fluorescence GSA, 0.01 wt % Rhodamine B were added to the enzymes solution during the GSA preparation. The loading capacity (LC) and encapsulation efficiency (EE) of enzymes-encapsulated vesicles were determined by measuring the amount of non-encapsulated enzymes through BCA (bicinchoninic acid) protein assay and using enzyme-free vesicles as basic correction. LC and EE were calculated as LC=(A−B)/C, EE=(A−B)/A, where A was expected encapsulated amount of enzymes, B was the free amount of enzymes in the collection solution, and C was the total weight of the vesicles. The zeta-potential and size distribution were measured on the Zetasizer (Nano ZS; Malvern). The TEM images of GSA were obtained on a JEOL 2000FX TEM instrument.

Oxygen Consumption Rate Assay

Oxygen consumption rate (OCR) was determined by using MitoXpress (Cayman Chemical) according to the manufacturer's protocol. Briefly, 200 μL 5 mg/mL GSA solution with 0, 100 or 400 mg/dL glucose containing 10 μL of MitoXpress probe was placed in a 96-well plate, and the plate was measured on a microplate reader at the excitation/emission wavelength of 380/650 nm at 37° C. Each sample well was measured repetitively every 5 minutes, by taking two intensity readings at delay times of 30 μs and 70 μs and gate time of 30 μs. Obtained TR-F intensity signals for each sample well were converted into phosphorescence lifetime (μs) τ values as follows: τ=(70−30)/ln(F1/F2), where F1 and F2 are the TR-F intensity signals at delay times 70 μs and 30 μs. The resulting increasing lifetime τ reflects the oxygen concentration in each sample.

In Vitro Glucose-Responsive Studies of the GSA

To evaluate the glucose-responsive capability of GSA, GSA were incubated in 500 μL of PBS buffer (NaCl, 137 mM; KCl, 2.7 mM; $Na_2HPO_4$, 10 mM; $KH_2PO_4$, 2 mM; pH 7.4) with 100 μM NADPH and 5 μg/mL cytochrome c reductase. The α-amylose was first washed with ethanol and then added to the PBS solution (10 mg/mL). Various amounts of 45% glucose solution (Corning) were added to reach a final solution of various glucose concentration (0 mg/dL, 100 mg/dL, and 400 mg/dL). The mixture was incubated at 37° C. in a container with an oxygen concentration of 21% by regulation of a mass flow meter. At predetermined time intervals, the released enzymes were separated from GSA suspension by a centrifugation (10 kDa molecular mass cutoff, Millipore) at 14,000×g for 10 minutes. The concentration of residual enzymes encapsulated in GSA and the released enzymes separated from the GSA was examined using a Coomassie Plus protein assay. The $A_{595}$ was detected on an Infinite 200 PRO multimode plate reader (Tecan Group Ltd.), and the enzyme content was calibrated with the standard curve of the enzyme solutions. The glucose were further separated by a centrifugal filter (10 kDa molecular mass cutoff, Millipore) at pH 7.4 by centrifugation at 14,000×g for 10 minutes. The glucose concentration was determined by Glucose (GO) assay. Briefly, the samples were diluted properly, and then added with assay reagent for 30 minutes at 37° C. The reactions were stopped at 30-60 second intervals by adding 2.0 mL of 12 N $H_2SO_4$ into each tube. The absorbance was measured against the reagent blank at 540 nm. The glucose concentration were calculated from the standard curve. For plotting the UV-Vis absorption of GSA solution, the intensity was measured at an A of 330 nm at the set time. The far-UV CD spectra of the native and released AA and GA from GSA (1 μM) were analyzed by the CD spectrometer (Aviv).

Fabrication of GSA-Loaded MNs

The microneedle fabrication was carried out using 10 uniform silicone molds from Blueacre Technology Ltd. Each mold is characterized with 20×20 arrays of microneedle pyramid cavities machined by laser ablation. The needle cavity had a side length of 400 μm at the base, a height of 800 μm and a side length of 5 μm at the tip. After plasma cleaning the molds, 50 μL GSA solution was deposited onto the mold surface. It was then followed by vacuum (600 mmHg) treatment for 5 min to allow the GSA solution flow into the MN cavities and achieve desirable viscosity. Afterwards, the molds were transferred to a Hettich Universal 32R centrifuge for 20 minutes at 2000 rpm to compact GSA to the tips region. After the GSA layer completely dried, second layer of 0.5 mL 10 mg/mL α-amylose solution was fed to the mold and was fabricated using the same process. The mold surface then was pipetted with 300 μL m-HA solution (4 wt %) mixed with MBA (2 wt %) and photo initiator (0.5 wt %) followed by combination of vacuum and centrifugation. The process was repeated 3-4 times until m-HA layer was dried and no obvious bubbles arising from the mold cavities under vacuum condition. For the backing of the MN patch, a piece of 4 cm×10 cm silver adhesive tape was applied around the 2 cm×2 cm mold baseplate, and 3 mL HA (5 wt %) solution was added to the prepared micromold reservoir and dried at 25° C. (overnight in vacuum desiccator). After desiccation was completed, the microneedle patch was crosslinked through in situ polymerization under 30 s UV irradiation (wavelength of 365 nm). The resulting product was carefully separated from the mold and tailored to fit the homemade applicator. The final MNs can be stored in 4° C. within a sealed six well cell culture plate for a week.

Mechanical Strength Test

The mechanical strength of a MN was measured with a stress-strain gauge by pressing the needle against a stainless-steel plate on an MTS 30G tensile testing machine. The initial gauge was set as 2.00 mm between the MN tip and the stainless steel plate, with 10.00 N as the cell loading capacity. The speed of the top stainless-steel plate moving toward the MN was set as 0.1 mm·s$^{-1}$. The failure force of MN was recorded as the needle began to buckle.

Cell Culture

Mouse insulinoma cell line 6 (MIN6) cells were kindly provided by Dr. Michael McManus, University of California, San Francisco. The culture medium used was DMEM high glucose medium with fetal bovine serum (15%), penicillin/streptomycin (1%) and 2.5 uL of islet mercaptoethanol (Biorad) per 500 mL media at 37° C. and 5% CO2. Media was changed every 3 days and the cells were passaged at 60% confluency. The 32-38th passages of the MIN6 cell lines were used.

Encapsulation of Pancreatic β-Cells

An aqueous solution of 2 wt % alginate was centrifuged at 12 000 rpm to remove any impurities. The alginate (120 mg) solution was mixed with 1-ethyl-3-(3-(dimethylamino)propyl)carbodiimide (EDC)/N-hydroxysuccinimide (NHS) (50 mg/30 mg) in pH 5.0 acetic buffer for 30 minutes to activate carbonyl groups on alginate, followed by mixing with additional 1,6-diaminohexane (60 mg) for another 4 h.

Figure 15A:
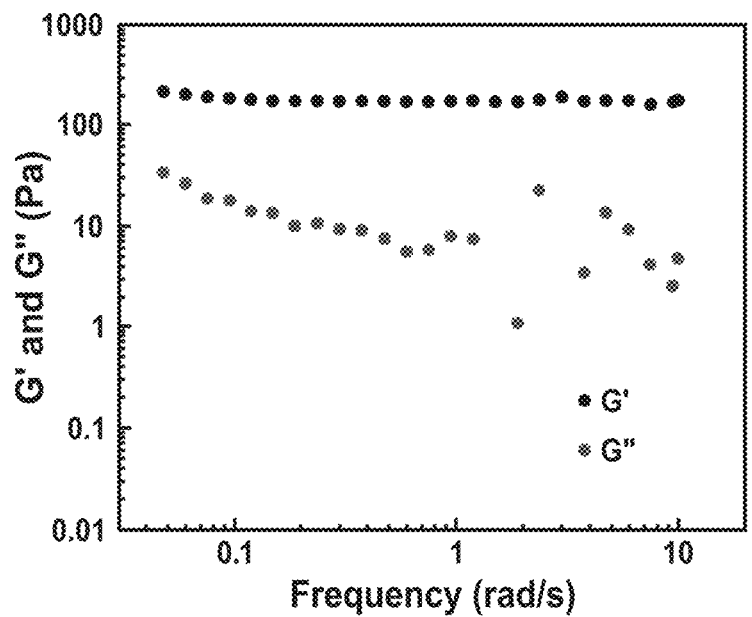
FIGS. 15A-B show rheological behavior of crosslinked m-HA hydrogel containing 98% complete cell growth medium at (a) 25° C. and (b) 37° C. using a TA Instruments AR-2000 stress controlled rheometer with sandpaper covered parallel-plate (25 mm). Experiments were performed within the linear viscoelastic regime at 0.5 Pa geometries with a 2 mm gap. Measurements were performed at least thrice to ensure reproducibility within ±10%.
Figure 15B:
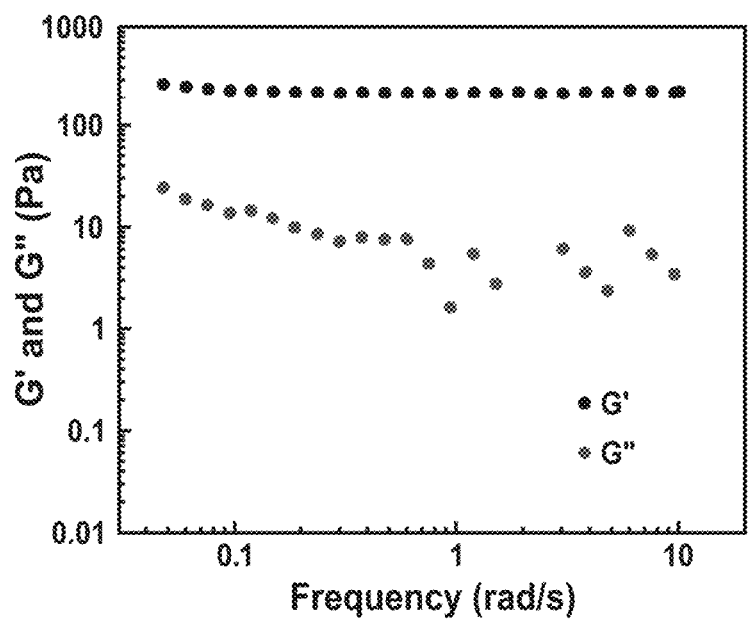

The mixture was precipitated in 2-propanol (IPA) to remove unreacted diamine. The alginate-amine derivative was reacted with the peptide sequence of CGRGDS (the weight ratio between peptide to alginate was 0.02:1) that has the Cys residue of free thiol in sodium bicarbonate solution (50 mM; pH=8.5) for 4 h at 4° C. The peptide-modified alginate was purified via extensive dialysis with deionized water for 5 d (3500 Da molecular mass cutoff, Millipore), sterilized through a 0.22-μm filter and lyophilized. MIN6 cells were trypsinized and suspended at ($2\times10^6$ cell/mL) in 2% alginate-RGD culture medium supplemented with 1% type IV collagen. The mixture was transferred into a 1 mL syringe with an attached blunt tip, 22 gauge metal needle. The syringe was placed in an electrospray system equipped with a syringe pump. The positive electrode of the electrospray system was connected to the needle, and the negative electrode was connected to a metal receiving container with 50 mL of 20 mM $BaCl_2$. The solution was sprayed at a 0.155 mL/min flow rate under a high voltage (8 kV) with a working distance of 5 cm to the receiving container. After droplets (50-65 uL) were extruded, the inner phase was gelatinized in sterilized $BaCl_2$ (200 mM) solution for 5 minutes. The collected capsules were then rinsed three times with sterilized NaCl solution (150 mM) before transferring to DMEM media in a 12 well culture plate. Homogeneous number of ~100 capsules were collected and further introduced into a bulk hydrogel for each experimental group to permit comparison across treatments. The HA hydrogel were crosslinked by photopolymerization of m-HA in DMEM (2%, wt %, DMEM) with N,N'-methylenebisacrylamide (MBA 2%, wt %) and photoinitiator (Irgacure 2959; 0.05%, w %) via UV irradiation (wavelength: 365 nm) for 1 minute (FIG. 15).

Characterization of Pancreatic β-Cell Capsules

To analyze the morphological characteristics of cellular clusters, the pancreatic β-cell capsules were viewed under Olympus IX70 multi-parameter microscope. The average diameter of the pancreatic β-cell capsules was fitted to an ellipse and analyzed by adjusting the images using the particle analyzing method of the ImageJ software.

Qualitative cell viability was visualized by the LIVE/DEAD Viability/Cytotoxicity Kit (Invitrogen). Cell capsules were incubated in PBS (NaCl, 137 mM; KCl, 2.7 mM; $Na_2HPO_4$, 10 mM; $KH_2PO_4$, 2 mM; pH 7.4) with 4 μM calcium AM and 8 μM ethidium homodimer-1 for 1 hour. Capsules were then rinsed in PBS to remove the excess staining solution and fixed with 2% paraformaldehyde for 15 minutes. The capsules were placed on a glass slide and imaged via Leica DM5500B Fluorescent Microscope equipped with a digital camera and the compatible LAS-AF software. Viability was quantified by counting the number of live (green) (excitation, 494 nm; emission, 517 nm) and dead (red) (excitation, 528 nm; emission, 617 nm) cells.

Characterization of Glucose-Responsive System (GRS)

The morphology of the MN patch was characterized using SEM. The microneedles along with their bases were attached to an SEM sample stub using a double-stick carbon tab. The samples were coated with a 7 nm thick gold-palladium layer using an EmTech Turbo EM sputter coater. Imaging was carried out on a FEI Verios 460L field-emission scanning electron microscope (FESEM) at the Analytical Instrumentation Facility, North Carolina State University. Calcium AM-stained pancreatic β-cell capsules were positioned on the back of a MN patch loaded with rhodamine-labeled GSA. The fluorescence image was taken from side view of the L-S GRS by Olympus IX70 multi-parameter fluorescence microscope.

Glucose Stimulated Insulin Secretion

Functional assessment of encapsulated cells was tested via static glucose-stimulated insulin secretion (GSIS) assay. 2-3 days before the experiment, $2\times10^5$ MIN6 cells were seeded per 96 well plate (Corning Costar). Similar to the 2D cell culture, same amount of cells in 3D capsules were cultured in 96 well plate (10/each well) 1 days prior to glucose treatment. The Kerbs-Ringer (KRB) buffer (128 mM NaCl, 4.8 mM KCl, 1.2 mM $KH_2PO_4$, 1.2 mM $MgSO_4$, 2.5 mM $CaCl_2$, 10 mM HEPES, 0.1% (w/v)) supplemented with 0.1% BSA was prepared beforehand. The cells were incubated for 2h in KRB buffer BSA, at 37° C., 5% $CO_2$, and then incubated for 45 min with 100 mg/dL or 400 mg/dL glucose in the same condition. The amount of insulin secreted by the cells was quantified using a mouse insulin ELISA kit (Alpco.). The amount of insulin secretion in 400 mg/dL glucose containing KRB was normalized to insulin secreted in 100 mg/dL glucose containing KRB and expressed as insulin secretion index.

Immunofluorescence Imaging

Six hours after encapsulation, the cells were fixed in 4% paraformaldehyde at 4° C. and then embedded in OCT compound (Sakura Finetek) and flash-frozen in an isopentane bath on dry ice. The frozen cell capsules were sectioned (5-μm thickness), mounted on microscope slides, and stored at −80° C. For staining of insulin with immunofluorescence, the slides were washed twice, permeabilized for 30 min using a 0.1% Triton X100 solution, and subsequently blocked for 1 hour using a 1% bovine serum albumin (BSA) solution. After blocking, primary rabbit monoclonal to insulin antibody (abcam 181547) at 1/200 dilution was applied overnight at 4° C., followed by washing and incubation with secondary antibody goat anti-rabbit IgG (Alexa Fluor® 488) (abcam 150077) at 1/400 dilution (green). Slides were washed thrice, applied with cell permeant dye DAPI to stain the cell nucleus and covered with coverslips. Samples were imaged using the Olympus IX70 multi-parameter fluorescence microscope and processed using ImageJ software.

In Vitro Glucose-Responsive Studies of the GRS

Release of insulin from the MNs was performed using a microfluidics device as a lab-on-chip simulation of blood circulation system. To dynamically evaluate the glucose-responsive capability, the MN patch was placed in the open center of the microfluidic channel while the release media flowing through the needle tips (pH 7.4 KRB with various glucose concentration). The infusion and withdraw rates were set at 50 μL/min on two separate syringe pumps (Harvard Apparatus PHD 2000, Holliston, Mass.). The insulin release rate was quantified using a mouse insulin ELISA kit (Alpco.). The insulin content was measured at 450 nm on the Infinite 200 PRO multimode plate reader (Tecan Group Ltd., Switzerland), and calibrated with an insulin standard curve.

In Vivo Studies Using STZ-Induced Diabetic Mice

The in vivo efficacy of MN patches for diabetes treatment was evaluated on STZ-induced adult diabetic mice (male C57B6, Jackson Lab, U.S.A.). The animal study protocol was approved by the Institutional Animal Care and Use Committee at North Carolina State and University and University of North Carolina at Chapel Hill. The plasma-equivalent glucose was measured from tail vein blood samples (~3 µL) of mice using the Clarity GL2Plus glucose meter (Clarity Diagnostics, Boca Raton, Fla.). Their BGLs were monitored for two days before administration, and all mice were fasted overnight before administration. Five mice for each group were selected to be subcutaneously treated with MNs containing empty MNs without GRS (w/o GRS), MNs integrated with only L-GRS (L-GRS), MNs integrated with only S-GRS (S-GRS), MNs integrated with L-S-GRS (L-S GRS), MNs integrated with L-S-GRS but without GOx in S-GRS (L-S GRS (w/o GOx)), and MNs integrated with L-S-GRS but without $\alpha$-amylose in S-GRS (L-S GRS (w/o AM)). MN patches were applied on the dorsum skin by a homemade applicator with 5 N/patch for 10 min. The patch was fixed on the skin for sustained release using skin affix surgical adhesive. A 12 mm×12 mm×5 mm customized PDMS mold was covered on the patch. Inside the PDMS mold, pancreatic β-cells capsules were embedded in a cross-linked m-HA hydrogel made from DMEM for nutrients supply. For the MN (S-GRS), MN (w/o GRS) groups, no cells were incorporated into the devices. The BGLs of administrated mice in each group were then continuously monitored (at 5, 15, 30, and 60 minutes, and once per hour afterward). A glucose tolerance test was conducted to confirm the in vivo glucose responsiveness of MNs 2 h post-administration of MNs. Briefly, mice were fasted overnight and administered with L-S GRS. When the mice glucose levels reached the lowest at 2 hours post administration, mice were given 1.5 g glucose/kg (45% sterile glucose solution, corning cellgro) via i.p. injection. The glucose tolerance tests on healthy mice was conducted as controls. Blood was drawn from the tail vein, and glucose levels were measured using a glucometer at 0, 10, 20, 30, 40, 60, 90, and 120 minutes after glucose administration. Similarly, to assess the risks of hypoglycemia, two groups of healthy mice were administered with MN (L-S GRS) or MN (w/o GRS), but were not subjected to a glucose challenge.

Biocompatibility Study

Cell proliferation analysis was performed using a colorimetric methyl thiazolyl tetrazolium (MTT) assay. MIN6 cells were seeded into 96-well plates at a density of 5,000 cells per well and cultivated in 100 µL of DMEM. The plates were then incubated in 5% $CO_2$ and at 37° C. for 12 hours to reach 70-80% confluency before addition of serial dilutions of the dissolved MN solution. After incubation for 24 hours, the cells were washed with KRB solution and incubated with 100 µL fresh FBS free DMEM and fresh prepared 20 µL 3-(4,5-dimethylthiazol-2-yl)-2,5-diphenyltetrazolium bromide solution (MTT solution, 5 mg/mL). The plates were incubated for an additional 4 hours. After that, the culture media was carefully removed and then followed by the additional of 150 µL dimethyl sulfoxide (DMSO). The absorbance of the plates was read at 590 nm and a reference wavelength of 620 nm using a microplate reader (Infinite M200 Pro, Tecan, Morrisville, N.C., USA) within 10 minutes.

To evaluate the biocompatibility of MN patch in the mouse model. On day 2 post-administration, mice were euthanized by $CO_2$ asphyxiation and the surrounding tissues were excised. Mice with PBS administration were used as negative control. The tissues were fixed in 10% formalin and then embedded in paraffin, cut into 50-µm sections, and stained using H&E for histological analysis.

Statistical Analyses

Data are presented as means±SD. Statistical analysis was performed using the student t test or an ANOVA test. With a P≤0.05, the difference between experimental groups and control groups were considered statistically significant.

REFERENCES

[1] J. E. Shaw, R. A. Sicree, P. Z. Zimmet, Diabetes Research and Clinical Practice 2010, 87, 4; B. Belgium, IDF Diabetes Atlas, 6th edn, International Diabetes Federation 2013.
[2] M. C. James A. Matriano, Juanita Johnson, Wendy A. Young, Margaret Buttery, Kofi Nyam, Peter E. Daddona, Diabetes Care 2013, 36 Supply 1, S67; R. A. Hayward, Jama 1997, 278, 1663; D. R. Owens, B. Zinman, G. B. Bolli, The Lancet 2001, 358, 739.
[3] R. Mo, T. Jiang, J. Di, W. Tai, Z. Gu, Chemical Society Reviews 2014, 43, 3595.
[4] S. Schneider, P. J. Feilen, F. Brunnenmeier, T. Minnemann, H. Zimmermann, U. Zimmermann, M. M. Weber, Diabetes 2005, 54, 687; F. B. Barton, M. R. Rickels, R. Alejandro, B. J. Hering, S. Wease, B. Naziruddin, J. Oberholzer, J. S. Odorico, M. R. Garfinkel, M. Levy, F. Pattou, T. Berney, A. Secchi, S. Messinger, P. A. Senior, P. Maffi, A. Posselt, P. G. Stock, D. B. Kaufman, X. Luo, F. Kandeel, E. Cagliero, N. A. Turgeon, P. Witkowski, A. Naji, P. J. O'Connell, C. Greenbaum, Y. C. Kudva, K. L. Brayman, M. J. Aull, C. Larsen, T. W. H. Kay, L. A. Fernandez, M. C. Vantyghem, M. Bellin, A. M. J. Shapiro, Diabetes Care 2012, 35, 1436; G. L. Warnock, D. M. Thompson, R. M. Meloche, R. J. Shapiro, Z. Ao, P. Keown, J. D. Johnson, C. B. Verchere, N. Partovi, I. S. Begg, M. Fung, S. E. Kozak, S. O. Tong, K. M. Alghofaili, C. Harris, Transplantation 2008, 86, 1762.
[5] S. Merani, C. Toso, J. Emamaullee, A. M. J. Shapiro, British Journal of Surgery 2008, 95, 1449; R. Nishimura, M. Goto, S. Sekiguchi, K. Fujimori, A. Ushiyama, S. Satomi, Transplantation Proceedings 2011, 43, 3239; A. R. Pepper, B. Gala-Lopez, R. Pawlick, S. Merani, T. Kin, A. M. J. Shapiro, Nature Biotechnology 2015, 33, 518.
[6] H. Zimmermann, S. G. Shirley, U. Zimmermann, Current Diabetes Reports 2007, 7, 314; E. Pedraza, M. M. Coronel, C. A. Fraker, C. Ricordi, C. L. Stabler, Proceedings of the National Academy of Sciences 2012, 109, 4245.
[7] C. C. Lin, K. S. Anseth, Proceedings of the National Academy of Sciences 2011, 108, 6380.
[8] O. Veiseh, J. C. Doloff, M. Ma, A. J. Vegas, H. H. Tam, Andrew R. Bader, J. Li, E. Langan, J. Wyckoff, W. S. Loo, S. Jhunjhunwala, A. Chiu, S. Siebert, K. Tang, J. Hollister-Lock, S. Aresta-Dasilva, M. Bochenek, J. Mendoza-Elias, Y Wang, M. Qi, D. M. Lavin, M. Chen, N. Dholakia, R. Thakrar, I. Lacík, Gordon C. Weir, J. Oberholzer, D. L. Greiner, R. Langer, D. G. Anderson, Nature Materials 2015, 14, 643.
[9] O. Veiseh, B. C. Tang, K. A. Whitehead, D. G. Anderson, R. Langer, Nature Reviews Drug Discovery 2014, 14, 45.
[10] N. Gurung, S. Ray, S. Bose, V. Rai, BioMed Research International 2013, 2013, 1; R. Gupta, P. Gigras, H. Mohapatra, V. K. Goswami, B. Chauhan, Process Biochemistry 2003, 38, 1599; L. Kandra, Journal of Molecular Structure: THEOCHEM 2003, 666-667, 487.

[11] J. Yu, Y. Zhang, Y. Ye, R. DiSanto, W. Sun, D. Ranson, F. S. Ligler, J. B. Buse, Z. Gu, Proceedings of the National Academy of Sciences 2015, 112, 8260.

[12] O. Veiseh, R. Langer, Nature 2015, 524, 39; Z. Gu, A. A. Aimetti, Q. Wang, T. T. Dang, Y. Zhang, O. Veiseh, H. Cheng, R. S. Langer, D. G. Anderson, ACS Nano 2013, 7, 4194; W. Tai, R. Mo, J. Di, V. Subramanian, X. Gu, J. B. Buse, Z. Gu, Biomacromolecules 2014, 15, 3495.

[13] S. Peat, W. J. Whelan, W. R. Rees, Nature 1953, 172, 158; J. F. Robyt, D. French, Archives of Biochemistry and Biophysics 1967, 122, 8; W. J. Whelan, P. J. Roberts, Nature 1952, 170, 748.

[14] A. J. Harvey, S. A. Kaestner, D. E. Sutter, N. G. Harvey, J. A. Mikszta, R. J. Pettis, Pharmaceutical Research 2010, 28, 107.

[15] J. E. Chung, S. Tan, S. J. Gao, N. Yongvongsoontorn, S. H. Kim, J. H. Lee, H. S. Choi, H. Yano, L. Zhuo, M. Kurisawa, J. Y. Ying, Nature Nanotechnology 2014, 9, 907; H. Yu, X. Qiu, S. P. Nunes, K.-V. Peinemann, Nature Communications 2014, 5.

[16] Y. Seki, T. Nakamura, Y. Okami, Journal of biochemistry 1970, 67, 389.

[17] R. J. Hickey, A. S. Haynes, J. M. Kikkawa, S.-J. Park, Journal of the American Chemical Society 2011, 133, 1517.

[18] L. M. Weber, K. N. Hayda, K. Haskins, K. S. Anseth, Biomaterials 2007, 28, 3004.

[19] S. P. Sullivan, D. G. Koutsonanos, M. del Pilar Martin, J. W. Lee, V. Zarnitsyn, S.-O. Choi, N. Murthy, R. W. Compans, I. Skountzou, M. R. Prausnitz, Nature Medicine 2010, 16, 915.

[20] D. H.-C. Chou, M. J. Webber, B. C. Tang, A. B. Lin, L. S. Thapa, D. Deng, J. V Truong, A. B. Cortinas, R. Langer, D. G. Anderson, Proceedings of the National Academy of Sciences 2015, 112, 2401.

[21] W. Yuan, H. Xiaoyun, W. Zaozhan, C. Lizhu, Z. Liu, W. Fei, L. Liangming Wei, Drug Design, Development and Therapy 2013, 945.

[22] S. Mitragotri, D. G. Anderson, X. Chen, E. K. Chow, D. Ho, A. V. Kabanov, J. M. Karp, K. Kataoka, C. A. Mirkin, S. H. Petrosko, J. Shi, M. M. Stevens, S. Sun, S. Teoh, S. S. Venkatraman, Y Xia, S. Wang, Z. Gu, C. Xu, ACS Nano 2015, 9, 6644; K. M. Bratlie, R. L. York, M. A. Invernale, R. Langer, D. G. Anderson, Advanced Healthcare Materials 2012, 1, 267.

The invention claimed is:

1. A device for transport of a material across a biological barrier of a subject comprising:
   a plurality of microneedles each having a base end and a tip, with at least one pathway disposed at or between the base end and the tip;
   a substrate to which the base ends of the microneedles are attached or integrated;
   at least one reservoir which is in connection with the base ends of the microneedles array, wherein the reservoir comprises an agent delivery system, wherein the agent delivery system comprises an agent to be transported across the biological barrier, or a means for producing an agent to be transported across the biological barrier, and a means for detecting a physiological signal from the recipient, wherein said means for producing an agent to be transported across the biological barrier and said means for detecting a physiological signal both comprise viable, cultured cells; and
   a signal amplifier system integrated within the microneedles, wherein the signal amplifier system comprises a component capable of amplifying the physiological signal from the recipient wherein the means for producing an agent to be transported across the biological barrier produces an agent, or changes the amount of agent produced, based on an amplified signal from the signal amplifier system.

2. The device of claim 1, wherein the agent delivery system comprises a feedback component, such that volume or amount of the agent to be transported across the biological barrier can be altered based on the physiological signal.

3. The device of claim 2, wherein the physiological signal from the recipient is insufficient to be detected by the feedback component without amplification from the signal amplifier system.

4. The device of claim 1, wherein the cells are pancreatic β cells or stem cell-differentiated human pancreatic cells.

5. The device of claim 1, wherein the reservoir is semipermeable.

6. The device of claim 1, wherein the reservoir comprises an alginate microgel.

7. The device of claim 1, wherein the reservoir comprises a therapeutic, prophylactic, or diagnostic agent.

8. The device of claim 7, wherein the agent is selected from the group consisting of peptides, proteins, carbohydrates, nucleic acid molecules, lipids, organic molecules, biologically active inorganic molecules, and combinations thereof.

9. The device of claim 8, wherein the agent is insulin.

10. The device of claim 7, wherein the biological substance is glucose.

11. The device of claim 1, wherein the physiological signal is a biological substance in the subject.

12. The device of claim 11, wherein the physiological response in the subject comprises physiological environment factors, including pH, temperature, blood glucose levels and other biomarkers.

13. The device of claim 1, wherein the signal amplifier system comprises self-assembled polymeric nanosized vesicles.

14. The device of claim 13, wherein the glucose signal amplifier comprises glucose oxidase, α-amylase, and glucoamylase.

15. The device of claim 1, wherein the signal amplifier system is in the tip of the microneedle.

16. The method of claim 1, wherein said viable, cultured cells are mammalian cells.

* * * * *

UNITED STATES PATENT AND TRADEMARK OFFICE
CERTIFICATE OF CORRECTION

PATENT NO. : 10,980,992 B2
APPLICATION NO. : 15/999770
DATED : April 20, 2021
INVENTOR(S) : Zhen Gu et al.

It is certified that error appears in the above-identified patent and that said Letters Patent is hereby corrected as shown below:

In the Specification

In Column 1, Line 12, before the "BACKGROUND OF THE INVENTION" section, please insert the following new paragraph:
--STATEMENT OF GOVERNMENT SUPPORT
This invention was made with government support under grant number TR001111 awarded by the National Institutes of Health. The government has certain rights in the invention.--

Signed and Sealed this
Twenty-eighth Day of February, 2023

Katherine Kelly Vidal
*Director of the United States Patent and Trademark Office*